(12) United States Patent
Garvey

(10) Patent No.: US 10,850,018 B2
(45) Date of Patent: Dec. 1, 2020

(54) TREATMENT FLUID PREPARATION SYSTEM

(71) Applicant: Ellen Medical Devices Pty Ltd, Newtown (AU)

(72) Inventor: Vincent Joseph Garvey, Colby (IM)

(73) Assignee: Ellen Medical Devices Pty Ltd., Newtown (AU)

( * ) Notice: Subject to any disclaimer, the term of this patent is extended or adjusted under 35 U.S.C. 154(b) by 0 days.

(21) Appl. No.: 16/065,649

(22) PCT Filed: Dec. 23, 2016

(86) PCT No.: PCT/IB2016/057963
§ 371 (c)(1),
(2) Date: Jun. 22, 2018

(87) PCT Pub. No.: WO2017/109760
PCT Pub. Date: Jun. 29, 2017

(65) Prior Publication Data
US 2018/0369470 A1    Dec. 27, 2018

(30) Foreign Application Priority Data
Dec. 24, 2015 (AU) .............................. 2015905395

(51) Int. Cl.
*A61M 1/28* (2006.01)
*B01D 1/28* (2006.01)
(Continued)

(52) U.S. Cl.
CPC ................ *A61M 1/166* (2014.02); *A61J 1/20* (2013.01); *A61M 1/1656* (2013.01);
(Continued)

(58) Field of Classification Search
CPC .......... B01D 1/02; B01D 1/28; B01D 1/2843; B01D 1/2846; B01D 1/2856;
(Continued)

(56) References Cited

U.S. PATENT DOCUMENTS 1,049,014 A * 12/1912 Weir ....................... B01D 1/02
159/28.4
2,339,862 A *  1/1944 Kleinschmidt ........ B01D 1/289
203/2
(Continued)

FOREIGN PATENT DOCUMENTS

CN        102874943      1/2013
JP        2012016683     1/2012
(Continued)

OTHER PUBLICATIONS

Casey et al., "The design of ultra-high-speed miniature centrifugal compressors", in European Conference on Turbomachinery Fluid Dynamics and Thermodynamics ETC 10, 2013.
(Continued)

*Primary Examiner* — Jonathan Luke Pilcher
(74) *Attorney, Agent, or Firm* — Knobbe Martens Olson & Bear LLP

(57) ABSTRACT

A system for purifying incoming fluid is modular and includes a heat exchanger module, an evaporator-condenser module and a compressor. The system components are arranged in a stacked configuration to facilitate gravitational flow of the purified fluid such that the purified fluid drains passively for collection. A system for preparation of ready-to-use treatment fluid includes the modular fluid purification system, a preparation station and a coupling device. The components are configured to be retained in a portable carrier that is manually operable for improved access to and mobility of the components. A coupling device can connect the flow channels of several components and can be used in
(Continued)

preparing ready-to-use dialysate. A system prepares a receptacle and a ready-to-use treatment fluid in the receptacle.

21 Claims, 13 Drawing Sheets

(51) Int. Cl.
*B01D 5/00* (2006.01)
*C02F 1/04* (2006.01)
*A61M 1/16* (2006.01)
*B01D 19/00* (2006.01)
*F04D 17/10* (2006.01)
*A61J 1/20* (2006.01)
*C02F 103/02* (2006.01)
*F04D 29/30* (2006.01)
*F04D 29/44* (2006.01)

(52) U.S. Cl.
CPC ........... *A61M 1/287* (2013.01); *B01D 1/2843* (2013.01); *B01D 1/2856* (2013.01); *B01D 5/006* (2013.01); *B01D 19/001* (2013.01); *C02F 1/041* (2013.01); *F04D 17/10* (2013.01); *A61J 2200/42* (2013.01); *A61J 2200/76* (2013.01); *A61M 1/28* (2013.01); *A61M 2205/3368* (2013.01); *A61M 2205/3389* (2013.01); *A61M 2205/3653* (2013.01); *C02F 2103/026* (2013.01); *F04D 29/305* (2013.01); *F04D 29/441* (2013.01)

(58) Field of Classification Search
CPC .... B01D 5/0057; B01D 5/006; B01D 5/0069; B01D 5/0075; A61M 1/28; A61M 1/287; A61M 1/166; C02F 1/041
See application file for complete search history.

(56) References Cited

U.S. PATENT DOCUMENTS

| | | | |
|---|---|---|---|
| 3,136,707 A | 6/1964 | Hickman | |
| 4,082,616 A * | 4/1978 | Antony | B01D 1/16 202/173 |
| 4,503,333 A | 3/1985 | Kulin et al. | |
| 4,516,971 A | 5/1985 | Spencer | |
| 4,610,469 A | 9/1986 | Wolff-Mooij | |
| 4,769,113 A | 9/1988 | Sears | |
| 5,372,709 A | 12/1994 | Hood | |
| 6,616,839 B1 | 9/2003 | Peterson et al. | |
| 8,034,235 B2 | 10/2011 | Rohde et al. | |
| 10,011,502 B2 * | 7/2018 | Zebuhr | B01D 3/28 |
| 2003/0153865 A1 | 8/2003 | Connell et al. | |
| 2004/0050503 A1 * | 3/2004 | Vallejo-Martinez | B01D 1/22 159/22 |
| 2004/0120802 A1 | 6/2004 | Sanchez et al. | |
| 2005/0015070 A1 | 1/2005 | Delnevo et al. | |
| 2005/0051418 A1 * | 3/2005 | Lama | B01D 1/10 203/21 |
| 2007/0080172 A1 | 4/2007 | Tyrrell et al. | |
| 2008/0105529 A1 | 5/2008 | Burke et al. | |
| 2010/0200388 A1 | 8/2010 | Ward | |
| 2012/0006670 A1 | 1/2012 | Kamen et al. | |
| 2013/0092361 A1 | 4/2013 | Wrazel et al. | |
| 2013/0175155 A1 * | 7/2013 | Lee | B01D 1/28 202/185.1 |
| 2013/0186741 A1 | 7/2013 | Batty et al. | |
| 2014/0334974 A1 | 11/2014 | Rasooly et al. | |
| 2016/0002065 A1 * | 1/2016 | Zebuhr | B01D 1/065 203/10 |

FOREIGN PATENT DOCUMENTS

| | | |
|---|---|---|
| JP | 2013094754 | 5/2013 |
| RU | 2323893 | 5/2008 |
| WO | WO 99/20249 A1 | 4/1999 |
| WO | WO 2011/127573 A1 | 10/2011 |

OTHER PUBLICATIONS

Donner., "First Annual Progress Report", unclassified AD 296 847, Armed Services Technical Information Agent, Arlington, Virginia, USA.
International Preliminary Report on Patentability received in PCT Application No. PCT/IB2016/057963, dated Jun. 26, 2018.
International Search Report received in PCT Application No. PCT/IB2016/057963, dated May 10, 2017.
International-Type Search Report received in Australian Application No. 2015905395, dated Nov. 25, 2016.
Written Opinion received in PCT Application No. PCT/IB2016/057963, dated May 10, 2017.
Examination Report in European Patent Application No. 16826472.9 dated Jun. 12, 2020.
Examination Report in Indian Patent Application No. 201837025844 dated Jul. 13, 2020.
Office Action in Chinese Patent Application No. 201680082403.2 dated May 9, 2020.

* cited by examiner

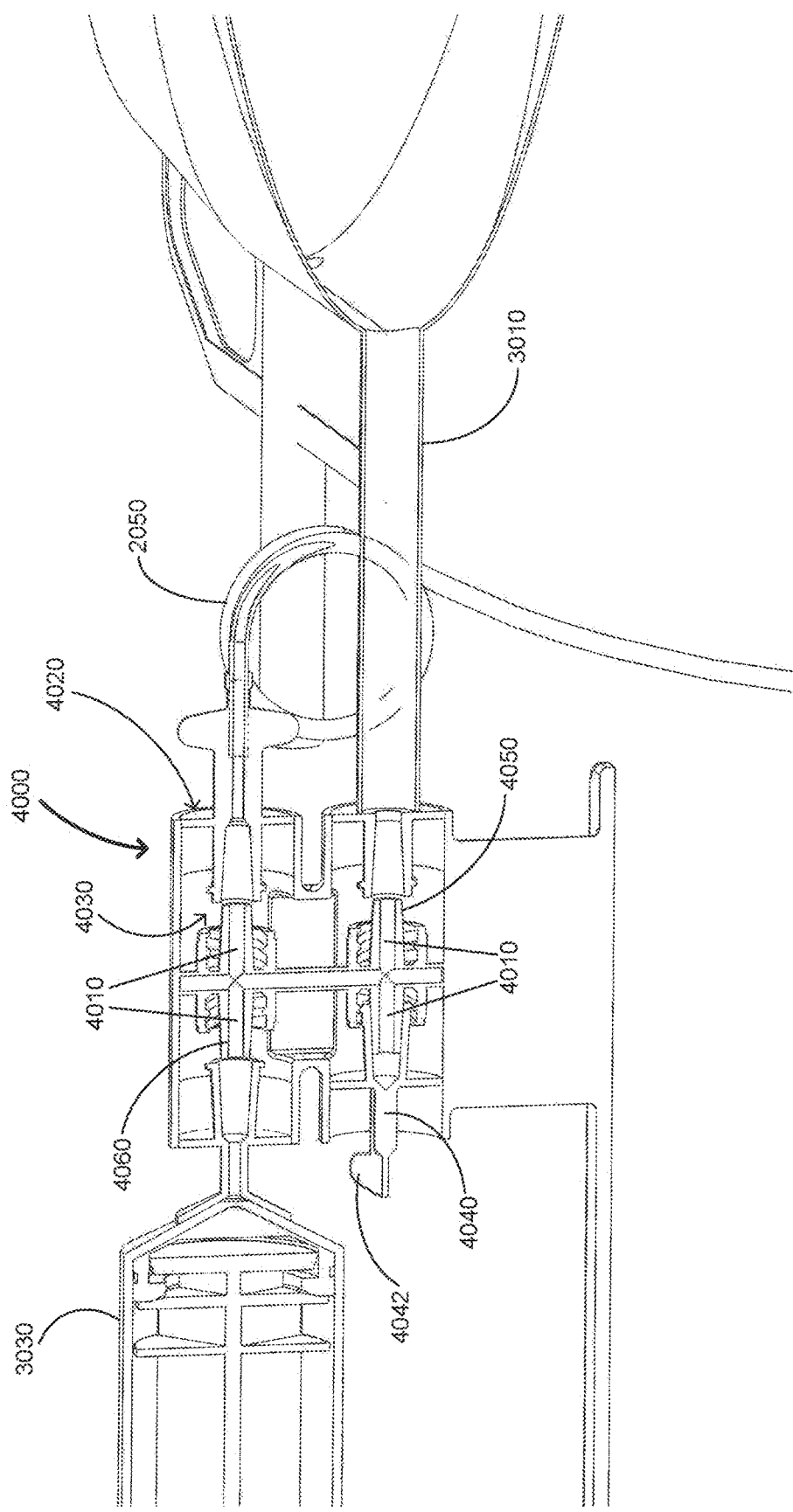

TREATMENT FLUID PREPARATION SYSTEM

CROSS-REFERENCE TO RELATED APPLICATIONS

This application is the U.S. National Phase under 35 U.S.C. § 371 of International Application No. PCT/IB2016/057963, filed Dec. 23, 2016, designating the U.S., and published in English as WO 2017/109760 A1 on Jun. 29, 2017, which claims priority to Australian Application No. 2015905395, filed Dec. 24, 2015, the entire contents of which are incorporated herein by reference.

TECHNICAL FIELD

The present invention relates to a system for purifying a fluid such as water to make it suitable for use in the preparation of and delivery of dialysate to a patient requiring dialysis. It relates particularly but not exclusively to a small, efficient, robust and lightweight system that enables more affordable and convenient dialysis, particularly peritoneal dialysis. The present invention also relates to complimentary means of preparing dialysate using the purified fluid and of delivering dialysate to a patient requiring dialysis.

BACKGROUND OF INVENTION

Kidney failure (also known as end-stage kidney disease) occurs when the kidneys are unable to adequately remove waste from the blood and control the level of fluid in the body. People with kidney failure require dialysis or kidney transplant to stay alive. Dialysis treatment is not accessible to many patients due to cost or location. Moreover, such treatment usually restricts patient mobility and travel options.

Kidney dialysis is commonly provided by either Haemodialysis (HD) or Peritoneal Dialysis (PD). For haemodialysis, surgical placement of a fistula is required to provide means for circulating the patient's blood through the external dialysis machine. This machine behaves like an artificial kidney and includes a membrane dialysis exchanger and pumps to circulate dialysate and blood through the exchanger. The machine used in haemodialysis is expensive, and requires sophisticated support in terms of consumables, operation and maintenance. Moreover, the patient is substantially immobile during treatment.

Peritoneal dialysis does not require the patient's blood to be circulated externally through an artificial kidney. In peritoneal dialysis, a catheter carrying dialysate is inserted in the abdomen. The inside lining of the abdomen (the peritoneum) acts as a natural filter or membrane which allows excess fluids and waste products to pass from the blood stream into the dialysate. Dialysate remains in the abdomen for a "dwell time" after which used dialysate is drained and expelled. Thus, waste products normally excreted in urine are expelled in waste dialysate. PD can be administered as Continuous Ambulatory Peritoneal Dialysis (CAPD) or Automated Peritoneal Dialysis (APD). APD is a type of peritoneal dialysis in which a machine performs the fluid exchanges overnight while the patient sleeps. CAPD is a simpler type of peritoneal dialysis where the patient undergoes 3 to 4 manually controlled dialysis treatments per day.

An advantage of peritoneal dialysis is that it can be self-administered, without the need for a dialysis machine, which is necessary for HD. Since the requirement to attend a clinic or hospital is removed, patients have access to greater mobility and this can provide other benefits such as improved quality of life and productivity. Additionally, peritoneal dialysis can be daytime/ambulatory or nocturnal providing further improvements in mobility.

The cost and availability of consumables, particularly dialysate, can be a limiting factor in the uptake of home dialysis, particularly for patients in remote or disadvantaged locations. Commonly, dialysate is prepared by mixing dialysate concentrate with pure water. At a care facility with a central pure water supply, the water is delivered to the point of treatment and mixed with dialysate concentrate by the dialysis machine. For PD patients, pre-mixed dialysate is distributed in bags for direct use. In some cases, the mixed dialysate may be prepared by the patients themselves (home dialysis). However, few patients requiring dialysis have access to water having sufficient purity (e.g. for PD use, equivalent or similar to Water For Injection (WFI)). The purity of water used in preparation of dialysate for PD, and indeed the sterility of the procedure in preparing and delivering the dialysate is important because unlike haemodialysis which provides a membrane filter outside the patient's body as a first barrier to microbial particles, there is no such barrier in peritoneal dialysis. Rather, the dialysate is delivered directly into the abdomen, and is therefore specified to a higher level of purity.

Up to 12 litres of dialysate may be required daily for PD patients. If delivered monthly, approximately 400 kg including other consumables and essential sterility maintaining material (tubes, caps, disinfectant, etc.) is required. The logistics associated with delivering and storing such a quantity of medical products are complex and expensive.

It would be desirable to provide a system that enables improved access and mobility for patients requiring peritoneal dialysis. In a preferred embodiment, such a system would enable safe, sterile preparation of dialysate with minimal energy consumption, and using any water source that is available. Ideally, the energy requirements of such a system would be sufficiently low, that mains power is not required, enabling access to operation of the system in very remote areas without access to mains electricity and/or potable water.

The discussion of the background to the invention included herein including reference to documents, acts, materials, devices, articles and the like is included to explain the context of the present invention. This is not to be taken as an admission or a suggestion that any of the material referred to was published, known or part of the common general knowledge in Australia or in any other country as at the priority date of any of the claims.

SUMMARY OF INVENTION

Viewed from one aspect, the present invention provides a system for purifying incoming fluid, the system being modular and comprising: (a) a heat exchanger module; (b) an evaporator-condenser module; and (c) a compressor; wherein the system is configured to facilitate passive drainage of the purified fluid for collection, and wherein the above components are arranged in a stacked configuration to facilitate gravitational flow of the purified fluid such that the purified fluid drains passively for collection.

In some embodiments, connections between the modular components are disposed vertically to minimise fluid retention in the system during gravitational flow.

Ideally, the heat exchanger module has a housing containing a thermally conductive coiled tube, typically a planar (e.g. spiral) coiled tube, but could usefully be an axial (e.g.

helix) coiled tube. Preferably, the coiled tube is a single continuous tube arranged within the housing in a planar coil. The housing also defines a first chamber containing a heater and receiving a vertically disposed conductive tube carrying pressurised vapour from the compressor. The heater may be e.g., an electrically resistive heater.

In some embodiments, the vertically disposed tube has an outlet in the form of a small hole or nozzle for injecting pressurised vapour into the chamber to degas fluid in the first chamber. Typically, the pressurised vapour is injected into a columnar portion of the first chamber.

In some embodiments, the vertically disposed tube extends through the evaporator-condenser module and also delivers pressurised vapour into a condenser tube of the evaporator-condenser module.

Ideally, one or more chambers of the system include a fluid level sensor or means for determining a fluid level particularly in a chamber of the evaporator-condenser module and condensate level. In some embodiments, the first chamber includes a fluid level sensor used to maintain a fluid level covering the heater. The fluid level sensor may be operatively connected to a fluid inlet controller configured to control the rate of incoming fluid flow into the heat exchanger module.

Preferably, the evaporator-condenser module has a housing and a thermally conductive coiled or folded (or e.g. arranged in a zig-zag) condenser tube arranged within the housing such that in operation, the condenser tube is partially immersed in fluid in the housing. Latent heat transfer from vapour inside the condenser tube to fluid in the housing causes the fluid to boil thus assisting agitation of the liquid to cause splashing and wet the condenser tube outer surface which in turn evaporates to form vapour. Preferably, the condenser tube is a single continuous tube arranged within the housing in a planar coil.

In some embodiments, the evaporator-condenser module includes one or more nozzles configured to inject pressurised vapour from the compressor into the housing. The pressurised vapour may be injected from the compressor via the condenser tube into the housing. Ideally, a plurality of the nozzles are spaced around a periphery of the condenser tube within the evaporator-condenser housing and situated below a fluid level in the housing during operation. The plurality of nozzles may be connected to a steam injection tube and evenly spaced apart. The steam injection tube may be on the periphery of the condenser tube. This increases wetting of the condenser outer tube while permitting a lower operating fluid level. The plurality of nozzles may be angled such that the peripheral fluid spins in a direction causing fluid to be drawn along the spiral shape towards the centre of the housing.

In some embodiments, one or more radially extending fluid flow channels are provided in the heat exchanger module housing and are configured to encourage fluid to return from the centre of the housing to an outer region of the housing.

Preferably, one or both of the heat exchanger module and the evaporator-condenser module is contained within a modular housing having a lower housing portion and an upper housing portion that are releasably couplable so as to facilitate access to surfaces of the module. The lower and upper housing portions may be releasably couplable by friction or snap lock fit. A seal between the upper and lower housing portions may be provided which is configured to be radially compressible to achieve fluid-tight closure of the housing when the upper and lower housing portions are coupled together.

Preferably, the heat exchanger module defines an incoming fluid flow channel formed by a void in a housing of the heat exchanger module. The void is positioned between an upper housing portion, a thermally conductive coiled tube and lower housing portion of the heat exchanger module. Connections may be arranged to provide a counterflow heat exchange effect. The construction of the heat exchanger module advantageously provides an incoming fluid flow channel without a dedicated conduit.

In some embodiments, the upper housing portion includes a grooved channel that together with the lower housing portion forms the void, which is confined by the outside of the thermally conductive tube. The thermally conductive coiled tube and grooved channel may be spiral-shaped such that the void is arranged as a closed spiral channel.

Preferably, the compressor is a centrifugal compressor having an impellor with a plurality of radial vanes of less than 2 mm radial height. A shroud is preferably affixed to the impellor such that during use, flow loss across the impellor vane walls is small. In some embodiments, the shroud has a shroud body and a radial collar extending away from the impellor, the radial collar having diameter of approximately 25% of the diameter of the shroud body.

In some embodiments, the compressor is a centrifugal compressor having a separately manufactured inducer comprised of elastomeric or compliant material. The inducer may have a blind bore adapted to mountingly receive an end portion of a shaft of the compressor motor. The blind bore may mountingly receive the end portion of the shaft through an interference or friction fit to the shaft, or the blind bore may include a threaded insert for engaging with a corresponding thread on the shaft. In the case of a threaded bore, the inducer may be made of a rigid material.

In some embodiments, the compressor includes a seal comprised of elastomeric material located between a casing and a turbine of the compressor, i.e. between the front casing and the shroud, to mitigate flow leakage therebetween.

In some embodiments, the compressor has inlet and outlet conduits configured to simultaneously provide vertical mounting means for mounting the compressor within the modular fluid purification system in the stacked configuration, typically without dedicated mounting means.

In some embodiments, the compressor includes a diffuser having a plurality of vanes for discharging diffused gas into a collector for exiting through an outlet conduit of the compressor, wherein the diffuser and collector are integrally formed.

In some embodiments, the system includes an evaporator level sensing chamber situated between the heat exchanger module and the evaporator-condenser module housing a fluid level sensor used to maintain a fill level within the evaporator-condenser module. Alternatively/additionally the system may include a condenser level sensing chamber situated between the heat exchanger module and the evaporator-condenser module housing a condensate fluid level sensor.

In some embodiments, the system includes a bleedoff (or blowdown) collector in the evaporator-condenser module configured to release from the evaporator-condenser module fluid to limit a concentration of solids in fluid circulating in the system. Ideally, the bleedoff tube uses a common conduit in the heat exchanger, such that there is only a single flow channel for the incoming water. This is in contrast to prior art systems in which usually two completely separate heat exchangers are required. Preferably, the rate of flow through the bleedoff collector is variable. The rate of flow through the bleedoff collector may be selected by a user according to one or more of a) a bleedoff rate as a fixed percentage of incoming fluid flow; b) incoming fluid quality; and c) geographic location of the purifier system having a known incoming fluid quality. In some embodiments the rate of flow through the bleedoff collector is changed by moving a bleedoff outlet up or down, preferably along a marked scale. Ideally, the bleedoff collector is in fluid communication with a secondary conduit in the heat exchanger module which is arranged such that thermal energy from bleedoff fluid is transferred to the incoming unprocessed fluid in the heat exchanger module, ideally in a manner which is thermally commensurate with the main processed fluid.

Preferably the system includes a controller configured to receive sensor data indicating one or more of: (a) a fluid level in the evaporator-condenser module; (b) a condensate fluid level; (c) fluid level in the heat exchanger module; and (d) temperature of outflow gas from the system; wherein the received sensor data is used in closed loop operation of the system in which sterility and positive flow are maintained.

A degassing module may be provided having a common gas discharge exit that combines gas from degassing that occurs in the heat exchanger module and gas output from the steam injection process during operation of the system. In some embodiments, the degassing module and heat exchanger module are integrally formed such that they share common housing components. In other embodiments, the degassing module, a portion of the heat exchanger and a portion of the evaporator-condenser module are integrally moulded such that they share common housing components.

In some embodiments, the system is further configured to be retained in a portable carrier including a bucket or container. The system may be further configured to be mounted on the portable carrier in an operating configuration. In this regard, the system may further include legs for mounting on a rim of the portable carrier. The legs may be foldable for retaining the system in the portable carrier in a stored configuration.

In some embodiments, the system further includes an insulating casing for minimising one or both of heat and noise loss to the ambient environment. Preferably, the system is operable from non-mains power selected from one of solar, wind or battery.

Viewed from another aspect, the present invention provides a system for purifying incoming fluid, the system being modular and comprising: (a) a heat exchanger module; (b) an evaporator-condenser module; and (c) a compressor; wherein the heat exchanger module defines an incoming fluid flow channel formed by a void in a housing of the heat exchanger module.

In some embodiments, the void is positioned between an upper housing portion, a thermally conductive coiled tube and a lower housing portion of the heat exchanger module. The upper housing portion may include a grooved channel that together with the lower housing portion forms the void, which is confined by the outside of the thermally conductive tube. The thermally conductive coiled tube and grooved channel may be spiral-shaped such that the void is arranged as a closed spiral channel.

Preferably, the thermally conductive coil tube is a single continuous tube arranged within the housing in a planar coil.

In some embodiments, the system further includes a degassing module, and wherein the degassing module and heat exchanger module are integrally formed such that they share common housing components.

Viewed from another aspect, the present invention provides a system for purifying incoming fluid, the system being modular and comprising: (a) a heat exchanger module; (b) an evaporator-condenser module; and (c) a compressor; wherein the evaporator-condenser module includes a thermally conductive condenser tube arranged within a housing of the evaporator-condenser module such that in operation, the condenser tube is partially immersed in fluid in the housing.

Preferably, the condenser tube is a single continuous tube is arranged within the housing in a planar coil.

In some embodiments, the evaporator-condenser module includes one or more nozzles configured to inject pressurised vapour from the compressor into the housing. A plurality of the nozzles may be spaced around a periphery of the condenser tube within the evaporator-condenser housing and situated below a fluid level in the housing during operation.

Viewed from another aspect, the present invention provides a system for purifying incoming fluid, the system being modular and comprising: (a) a heat exchanger module; (b) an evaporator-condenser module; and (c) a compressor; wherein the compressor is a centrifugal compressor having an impellor with a plurality of radial vanes and a shroud affixed to the impellor such that during use, flow loss across the impellor vane walls is minimised.

In some embodiments, the shroud has a shroud body and a radial collar extending away from the impellor, the radial collar having diameter of approximately 25% of the diameter of the shroud body. The plurality of radial vanes of the impellor may have a radial height of less than 2 mm. The compressor may have a separately manufactured inducer comprised of elastomeric or compliant material. The inducer may have a blind bore adapted to mountingly receive an end portion of a shaft of the compressor motor.

In some embodiments, the compressor includes a seal comprised of elastomeric material located between a casing and a turbine of the compressor to mitigate flow leakage therebetween.

In some embodiments, the compressor has inlet and outlet conduits configured to simultaneously provide vertical mounting means for mounting the compressor within the modular fluid purification system in a stacked configuration.

In some embodiments, the compressor includes a diffuser having a plurality of vanes for discharging diffused gas into a collector for exiting through an outlet conduit of the compressor, wherein the diffuser and collector are integrally formed.

Viewed from another aspect, the present invention provides a coupling device for use in connecting flow channels of a plurality of components and for use in preparing ready-to-use treatment fluid; the coupling device having a plurality of interconnected internal channels, each channel having a first coupling zone and a second coupling zone recessed in the channel relative to the first coupling zone, wherein each channel is configured for two stage connection with a respective component, the coupling device being configured for sterile interconnection of the flow channels of the plurality of components for passage of fluids therebetween.

The second coupling zone is recessed in the channel relative to the first coupling zone so as to e.g. mitigate physical contact with the second coupling zone.

Preferably, the first stage is a sterilisation stage in which respective ones of the components are in sealing physical contact with the first coupling zone but not with the second coupling zone; and the second stage is a coupling stage in which ones of the components are physically coupled with a respective one of the device channels at the sterilised second coupling zone. The first coupling zone may form a sealed chamber which encloses both of an inner surface (e.g. sterile) and outer surfaces (e.g. potentially exposed) forming the second coupling zone.

The coupling device ideally has at least three channels. One or more removable caps may be provided that are configured to occlude a channel in the coupling device. Ideally the removable caps have a handle portion for grasping the coupling device in an orientation that precludes steam burning or contamination during sterilisation. The handle may be located external to the first coupling zone.

The coupling device is preferably configured to protect both the first and second coupling zones from contamination. Preferably, the first coupling zone provides a steam sealing surface and the second coupling zone provides a fluid sealing surface. The first coupling zone may be arranged such that modest steam flow will prevent the ingress of ambient air.

In some embodiments, the treatment fluid may be selected from one of: (a) dialysate; or (b) intravenous (IV) fluid including diluted solutions of salt, glucose and/or sodium lactate.

Viewed from another aspect, the present invention provides a receptacle in the form of a sterile bag, pouch or container for receiving contents from the coupling device as described above. The receptacle may be provided with a second coupling device, configured for injection of steam into a first device coupled to the second device to determine if the receptacle is sufficiently sterile to be reused. For example, a detection means may be provided to detect that steam has permeated the system by evidence of steam exiting at a distal extremity from the inlet.

Viewed from another aspect, the present invention provides a system for preparation of ready-to-use treatment fluid, the system comprising: (a) modular fluid purification system; (b) a preparation station; and (c) a coupling device; wherein said components are configured to be retained in a portable carrier, and wherein the portable carrier is manually operable for improved access to and mobility of said components.

Preferably, the portable carrier is hand-held. The portable carrier may include a bucket or container and may have a handle portion for manual operation.

In some embodiments, the portable carrier defines walls of a chamber for storing unprocessed fluid which is fed to the modular fluid purification system by a submersible pump means. The modular fluid purification system may be supported above the stored unprocessed fluid in an operating configuration. The modular fluid purification system may be configured to be mounted on the portable carrier in the operating configuration. The modular fluid purification system may include legs for mounting on a rim of the portable carrier. The legs may be foldable for retaining the modular fluid purification system in the portable carrier in a stored configuration.

In some embodiments, the treatment fluid may be selected from one of: (a) dialysate; or (b) intravenous (IV) fluid including diluted solutions of salt, glucose and/or sodium lactate.

In some embodiments, the system further includes an insulating casing for the modular fluid purification system so as to minimise one or both of heat and noise loss to the ambient environment. The modular fluid purification system may be operable from non-mains power selected from one of solar, wind or battery.

Viewed from another aspect, the present invention provides a bulk concentrate storage device including a coupling device as described above, further including a valve therebetween.

Viewed from another aspect, the present invention provides a system for preparation of a receptacle and a ready-to-use treatment fluid in the receptacle, the system including: (a) a receptacle preparation module configured to prepare a receptacle containing a concentrate for the treatment fluid; and (b) a treatment preparation module configured to supply purified fluid to the receptacle for diluting the concentrate and providing a ready-to-use treatment fluid in the receptacle.

In some embodiments, the receptacle preparation module is positioned in a first location and the treatment preparation module is positioned in a second location, wherein the second location is at the point of use of the treatment fluid.

In some embodiments, the treatment preparation module is configured to supply the purified fluid from a modular fluid purification system.

In some embodiments, the treatment fluid may be selected from one of: (a) dialysate; or (b) intravenous (IV) fluid including diluted solutions of salt, glucose and/or sodium lactate.

In some embodiments, the receptacle preparation module is configured to: (a) form a receptacle from receptacle material; (b) at least partly fill the receptacle with a concentrate for the treatment fluid; (c) sterilise the concentrate filled receptacle; and (d) seal the sterilised receptacle. Prior to sealing the sterilised receptacle, the receptacle preparation module may be further configured to (e) reduce the volume of the sterilised receptacle.

In some embodiments, the receptacle preparation module is configured to form the receptacle having a portion with a connection for facilitating aseptic filling of the receptacle with the purified fluid. The treatment preparation module may be further configured to aseptically pierce the receptacle connection to supply the purified fluid. Alternatively, the treatment preparation module includes may include the coupling device as described above and be further configured to couple the receptacle connection with a conduit supplying the purified fluid.

In some embodiments, the concentrate and treatment fluid are respectively selected from one of: (a) dialysate concentrate and dialysate; or (b) salt, glucose and/or sodium lactate, and intravenous (IV) fluids.

Viewed from another aspect, the present invention provides a receptacle containing a concentrate for preparation of a ready-to-use treatment fluid, wherein the receptacle is configured to receive purified fluid supplied from a modular fluid purification system for diluting the concentrate in the receptacle and providing a ready-to-use treatment fluid in the receptacle.

In some embodiments, the receptacle includes a portion with a connection for facilitating aseptic filling of the receptacle with the purified fluid. The receptacle connection may be aseptically pierceable for supplying the purified fluid for filling of the receptacle. Alternatively, the receptacle connection may be couplable with a conduit supplying the purified fluid using the coupling device as described above for filling of the receptacle.

In some embodiments, the concentrate and treatment fluid are respectively selected from one of: (a) dialysate concentrate and dialysate; or (b) salt, glucose and/or sodium lactate, and intravenous (IV) fluids.

BRIEF DESCRIPTION OF DRAWINGS

The present invention will now be described in greater detail with reference to the accompanying drawings. It is to be understood that the embodiments shown are examples only and are not to be taken as limiting the scope of the invention as defined in the claims appended hereto.

FIG. 13 illustrates a coupling device according to an embodiment of the invention.

DETAILED DESCRIPTION

Fluid Purification System

The present invention provides a modular system 1000 for purifying fluid, the system 1000 comprising a heat exchanger module 1100, an evaporator-condenser module 1200 and a compressor 1300. The system 1000 is configured to facilitate passive drainage of the purified fluid for collection. The system components are arranged in a stacked configuration to facilitate gravitational flow of the purified fluid such that the purified fluid drains passively for collection.

Figure 1:
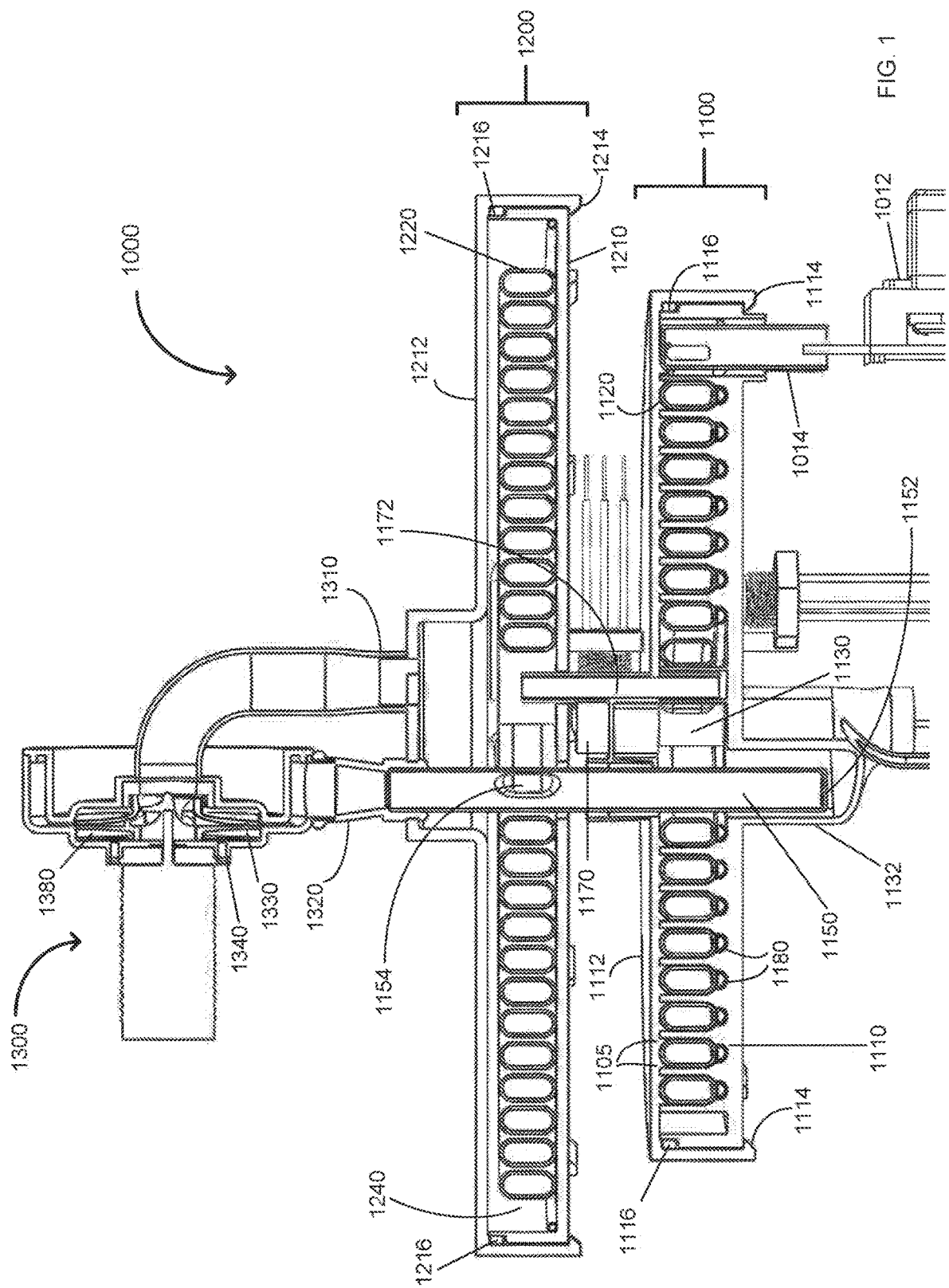
FIG. 1 illustrates in cross section a fluid purification system having a heat exchanger module, an evaporator-condenser module and a compressor arranged in a stacked configuration according to an embodiment of the invention.

FIG. 1 represents these features of the system 1000 according to an embodiment of the invention. In normal operation, an inlet pump 2020 (see FIG. 14) fills the lower housing 1110, 1210 of each module 1100, 1200, and condensing steam fills the condenser tube 1220 of the evaporator-condenser module 1200 and the heat exchange tube 1120 of the heat exchanger module 1100 with pressurised vapour from the compressor 1300, forcing the fluid through the system 1000. Advantageously, this produces gravitational/free-draining flow of purified condensate at the end of operation (even with all valves open, pumps deactivated etc.) It is understood that this has not been achieved in a fluid purification system until now.

The heat exchanger module 1100 consists mainly of a housing having a lower housing 1110 and an upper housing 1112, which is preferably circular, containing a thermally conductive coiled tube 1120 through which condensate from the evaporator-condenser module 1200 flows. The lower housing 1110 defines a chamber 1130 for receiving incoming fluid from the inlet pump 2020. The chamber 1130 includes a fluid level sensor 1160 (see FIG. 7) which is used for initial sterilisation as will be described in relation to "start-up" of the system below.

Figure 7:
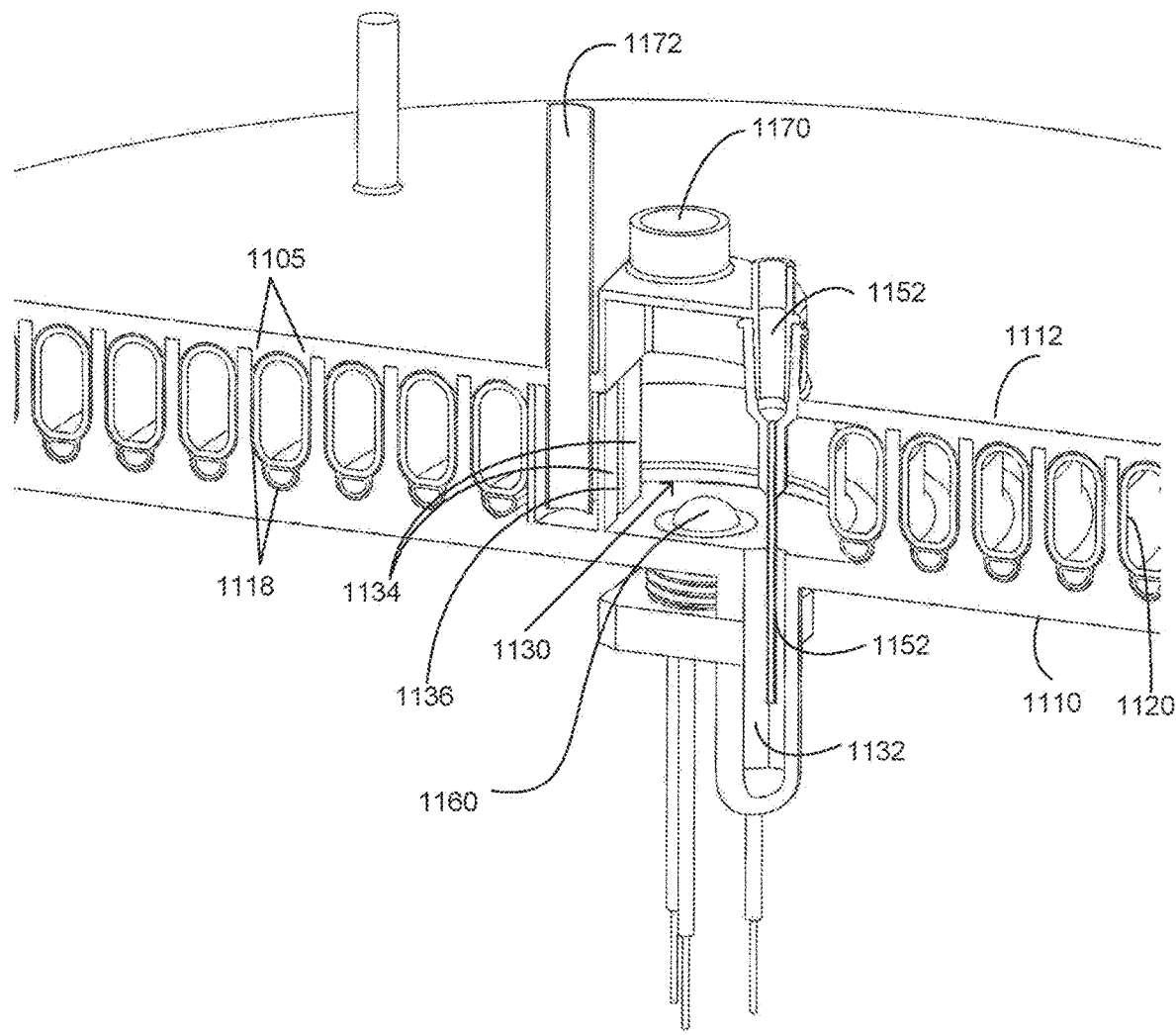
FIG. 7 illustrates features of a heat exchanger module facilitating degassing, according to an embodiment of the invention.

In normal operation, the incoming fluid from the inlet pump 2020 completely floods the chamber 1130 defined by lower housing 1110 of heat exchanger module 1100 and flows in a channel 1118 confined by the outside of the heat exchange tube 1120 and the upper and lower housings 1110, 1112 (see FIG. 7). The upper housing 1112 includes an interior groove or channel 1105, which is preferably spiral-shaped. The spiral groove 1105 and lower housing 1110 together form channel 1118, which is arranged as a closed spiral channel or slot surrounding the periphery of the heat exchange tube 1120. The incoming fluid flows through the narrow channel 1118, which in some embodiments is about 0.25 to 0.5 mm in width. The incoming fluid therefore has thermal contact with all of the surface area provided by the heat exchange tube 1120 for maximising heat transfer.

Figure 2:
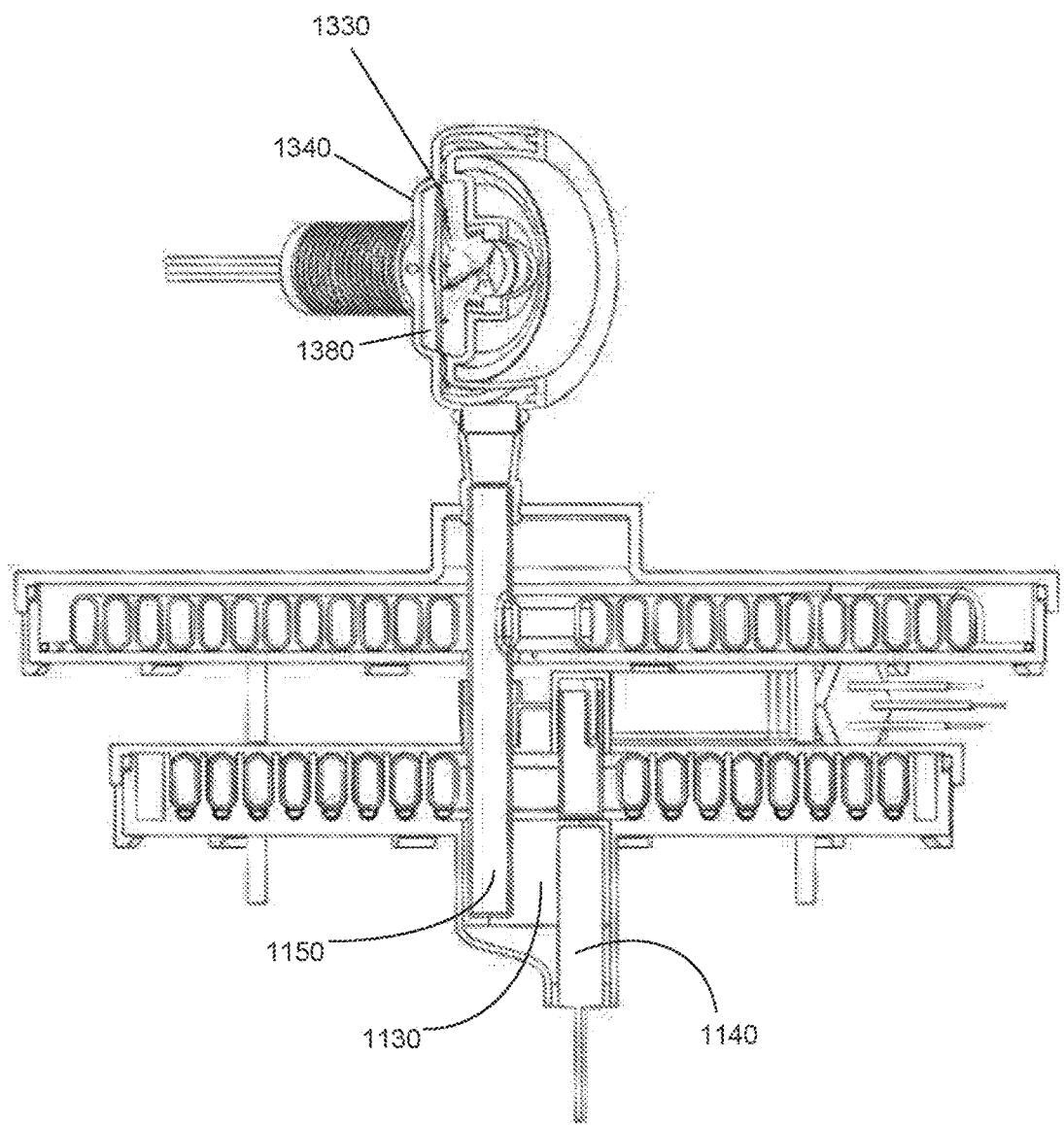
FIG. 2 is another view of the components in FIG. 1 showing a vertically disposed tube carrying superheated vapour according to an embodiment of the invention.
Figure 5:
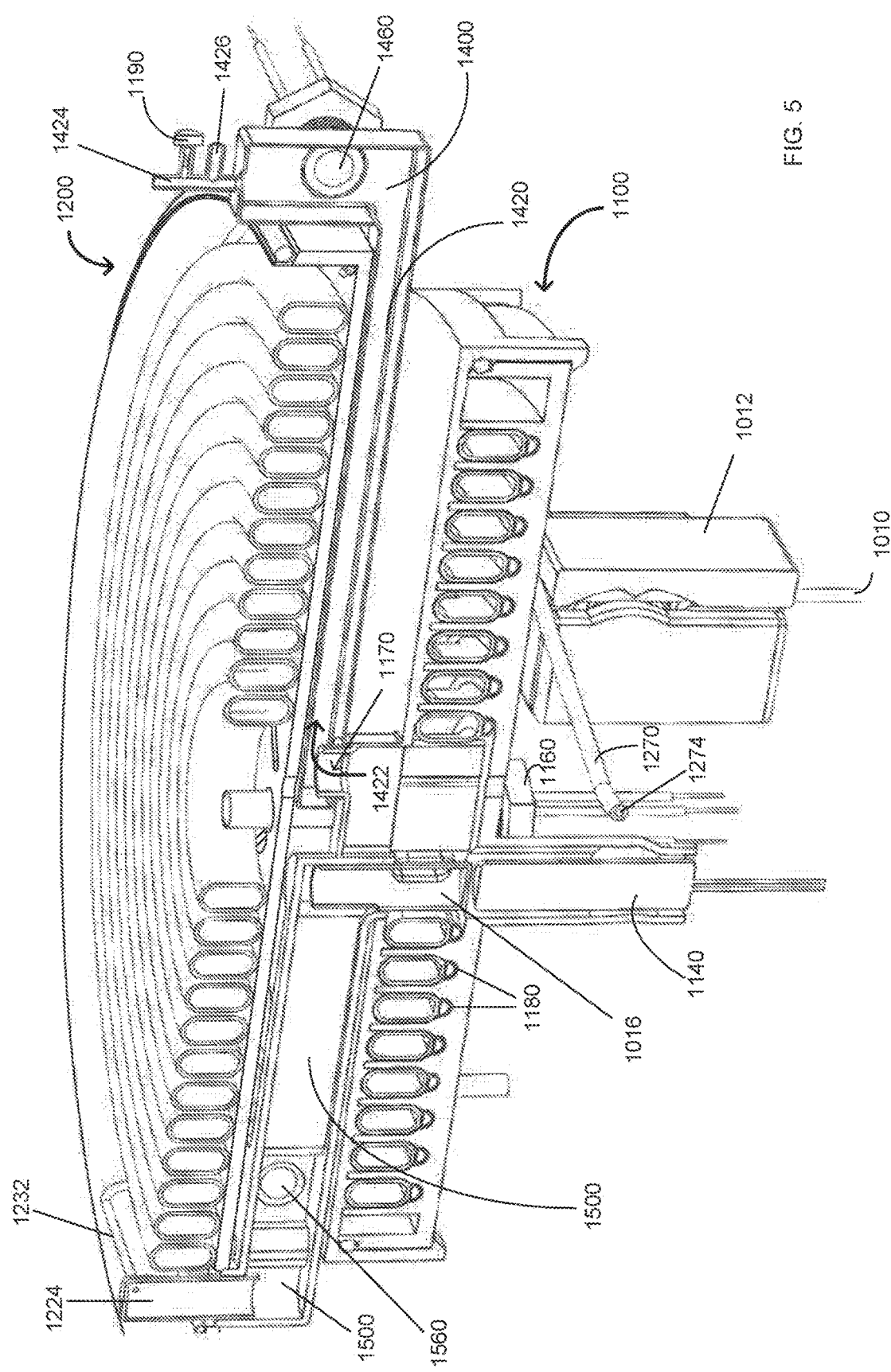
FIG. 5 illustrates in cross section a heat exchanger module and an evaporator-condenser module together with intermediate chambers for fluid level and temperature sensing, according to an embodiment of the invention.

The chamber 1130 includes a heater 1140 as shown in FIGS. 2 and 5. The incoming fluid also floods the chamber 1240 defined by the lower housing 1210 of the evaporator-condenser module 1200 up to about ⅓ the height of the chamber 1240. Also during normal operation, the heater 1140 of chamber 1130 is maintained at a temperature that is higher than the surrounding fluid in chamber 1130, warming the fluid to a vaporising temperature which for water is 100 C. Due to the location of heater 1140, the outer surface of the heat exchange tube 1120 is also heated. During heating, either along the outer surface of the heat exchange tube 1120 or in the chamber 1130 enclosing the heater 1140, dissolved solids in the fluid in the chamber 1130 and channel 1118 separate out and can collect as scale or sludge causing diminishing heat transfer from the heating surfaces (e.g. the surface of heater 1140 and outer surface of heat exchange tube 1120).

Accordingly, in preferred embodiments the heat exchanger module 1100 is constructed in a manner that is easily dismantled typically without the need for special tools so that the heat exchange coil 1120, the heater 1140 and the upper and lower housings 1112, 1110 can be cleaned. In one embodiment, the upper housing 1112 is snap-fit to lower housing 1110 by resilient tabs 1114 that can be flexed open by hand as shown in FIG. 1. Similarly, in preferred embodiments the evaporator-condenser module 1200 is easily dismantled so that the condenser tube 1220 and the upper and lower housings 1210, 1212 can be cleaned. The upper housing 1212 may also snap-fit to lower housing 1210 by resilient tabs 1214 as shown in FIG. 1, which can be flexed open by hand. Additionally/alternatively, the system 1000 as a whole may be easily dismantled such that the compressor 1300 may be readily disassembled from the evaporator-condenser module 1200, the evaporator-condenser module 1200 from the heat exchanger module 1100, and from other chambers such as the condensate level sensing chamber 1500 and evaporator level sensing chamber 1400 (see FIG. 5) in embodiments that include them.

Ideally, seals or O-rings 1116, 1216 provide gas-tight sealing between the upper and lower housings 1112, 1110 of the heat exchanger module 1100 and upper and lower housings 1212, 1210 of the evaporator-condenser module 1200. The seals or O-rings 1116, 1216 are radially compressed when the respective housings are closed to minimise the "clamping force" required to keep the housings closed. Thus, fasteners such as screws or bolts can be omitted.

Advantageously, the stacked configuration of the system 1000 enables a vertically disposed thermally conductive (e.g. copper or stainless steel) tube 1150 to deliver pressurised vapour from the compressor 1300 into a condenser tube 1220 in the evaporator-condenser module 1200, and into the chamber 1130 through a small opening 1152 or nozzle at the bottom of the tube 1150 (see FIG. 7). Since the outlet 1152 injecting pressurised vapour from the vertical tube 1150 into the chamber 1130 is very small, most of the vapour makes its way back to the condenser tube 1220.

Figure 10:
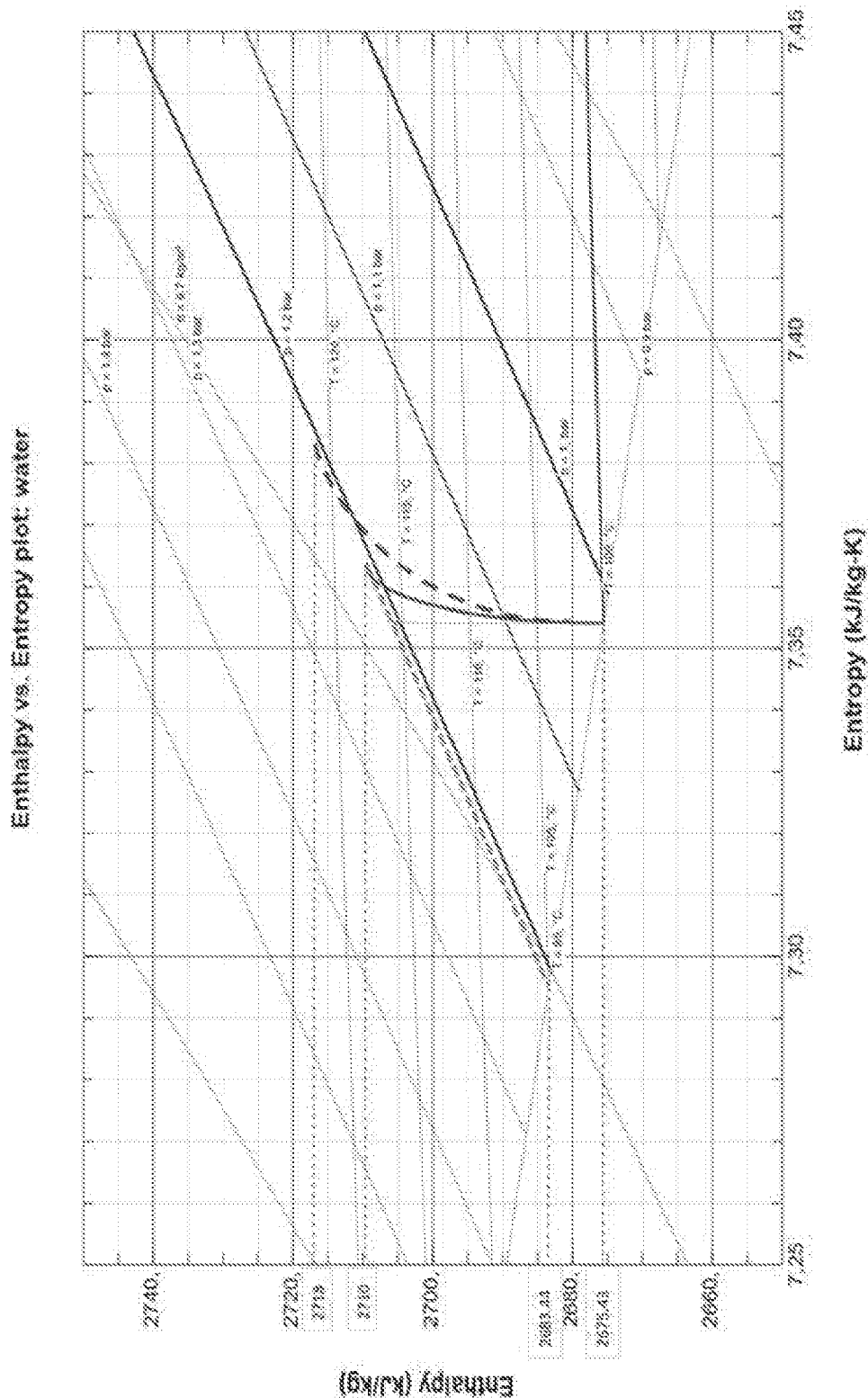
FIG. 10 is an enthalpy-entropy chart comparing the performance of prior art compressors utilising water as the compressor fluid.

The system 1000 employs a micro compressor 1300 in preferred embodiments so as to provide a portable fluid purification system. However, known micro scale compressors have low efficiencies when compared with the corresponding larger scale devices as is shown in FIG. 10 and described below. The inefficiencies of micro compressors can represent a significant proportion of the overall system energy. The inventor has therefore devised a means of recovering the lost energy.

In preferred embodiments, the vertical tube 1150 contains superheated vapour at approximately 118 to 125 C and more typically approximately 122 C. Ideally, as best shown in FIG. 2, the vertically disposed tube 1150 extends at least partially and more preferably, substantially the entire depth of the chamber 1130, thus causing the fluid in the chamber 1130 to boil by extracting thermal energy from the superheated vapour within the tube 1150. The vertical tube section 1150 is thermally conductive. Although the bulk flow of superheated vapour will enter the coiled condensing tube 1220 at a higher level through opening 1154 (see FIG. 1), contact with the tube walls combined with the turbulent flow in this region will be sufficient to transfer the superheated steam energy to the fluid, and cool the condensate (from 120-125 C) to saturation temperature (105 C). A further advantage of this arrangement is that heat delivered to this region directly reduces the heating requirement of heater 1140 thus saving energy. If the compressor 1300 operates with lower efficiency, the degree of superheating becomes greater. By recovering energy in this manner, it is possible to compensate for compressor inefficiencies and allow the use of a lower cost less efficient compressor without penalty to the overall system performance.

As fluid (e.g. water) in the chamber 1130 is heated, gases such as oxygen, nitrogen, carbon dioxide and others dissolved in the fluid have a lower threshold of absorption. The process of degassing can therefore rely on this principle of heating. When the fluid is water, which has a finite capacity for absorption, insertion of a gas for which water has a high affinity causes other residual gases to be displaced. Accordingly, pure steam may be utilised to increase the effectiveness of the degas process by causing residual gases dissolved in the fluid to come out of the solution in the form of bubbles. The degassing process is enhanced through the inventive system 1000 by injecting pressurised vapour from the compressor 1300 into the chamber 1130. The rising stream of vapour further heats the water in chamber 1130, driving bubbles of gas from the solution up to an exit or gas outlet 1170 (see FIGS. 1 and 7). The combined stream of vapour and gas rises and exits through the gas outlet 1170 which is in fluid communication with atmosphere either directly or indirectly through a gas outlet manifold. A non-return valve, in the form of a gravity sealing flap or ball, can be included in the gas outlet 1170 to prevent inflow of ambient air when the pressure in the chamber 1130 is lower than ambient air. The fluid thus degassed is directed through a dedicated degassed fluid outlet 1172 (see FIG. 7) and into the evaporator-condenser module 1200. Fluid also flows through an opening 1422 (see FIG. 5), however it is only for an initial period until a chamber 1400 is filled with fluid to a fluid level sensor 1460, after which no further fluid flows. In contrast, during normal operation the fluid flows through fluid outlet 1172 continuously as the water (at 100 C) is constantly evaporated by the surface of the condenser tube 1220, which is maintained at about 103.5 to 105 C by the vapour condensing inside.

The fluid level sensor 1160 is arranged within the housing 1110 as shown in FIG. 7, ideally within chamber 1130 such that it senses when the heater 1140 is covered with fluid. Ideally, sensor 1160 is operatively connected to a fluid or water inlet controller such as a valve or pump 2020 (FIG. 14) which controls the rate of flow into the heat exchanger module 1100 and provides control of fluid level when minimum cover of the heater 1140 is required (i.e. during start-up).

The evaporator-condenser module 1200 has a housing which is ideally circular and includes a lower housing 1210 and upper housing 1212 as shown in FIG. 1. A thermally conductive coiled condenser tube 1220 is arranged within the housing such that in operation, the condenser tube 1220 is partially immersed in fluid in the housing and latent heat transfer from vapour inside the condenser tube 1220 to fluid in the housing causes the fluid to boil and wet the condenser tube outer surface which in turn evaporates to form vapour. Ideally the condenser tube 1220 is arranged such that only a thin film of fluid is in contact with the outside tube wall facilitating the evaporation process. This ensures better evaporation performance than fully immersing the tube 1220 which leads to boiling and clinging of bubbles to the condenser tube outer surface, thus reducing the surface area exposed to fluid for evaporation. Maintaining a larger wetted tube surface optimises heat transfer. Preferably the fluid in the housing is degassed fluid from the heat exchanger module 1100. Preferably the condenser tube 1220 is a single continuous copper, stainless steel or other conductive tube, and preferably has a surface area of 0.15 to 0.2 $m^2$. (For example, a 10 mm diameter stainless steel (SS) tube would require a length of about 4.5 m, although any length that is suitable in the modular arrangement is contemplated). Multiple lengths of tube can be employed but a single continuous tube is preferred as problems can arise with joints and seals. Preferably, the condenser tube 1220 is oriented to preclude the purified liquid which condenses within the tube 1220 from pooling and obstructing vapour flow.

As outlined above, it is desirable for system 1000 to employ a micro compressor 1300 for portability. However, there are difficulties in designing a micro compressor, in particular one of centrifugal type. Firstly, at small flow rates, the axial tip velocities, particularly at modest rotational speeds are too low (in ratio to the radial velocities) to create an optimum pressure ratio. Secondly, once a reasonable pressure ratio is achieved, the leakage across the impeller (again, as a ratio of the small flow rate) results in significant losses which manifest as ever increasing outlet steam temperatures (superheat). The inventor has sought a means to mitigate both of these issues, and turn them to advantage. The first concept relates to allowing the compressor 1300 to operate at an increased volumetric flowrate of about 3 times the desired requirement, thus overcoming the first problem as described, and using the excess steam generated by the compressor 1300 to significantly improve the evaporator-condenser module 1200 performance. The second concept relates to converting the second problem as described to advantage by devising a way to transfer the "lost" energy to efficient use. The inventive solutions will now be described.

The compressor 1300 is in fluid communication with the evaporator-condenser module 1200. Compressor inlet 1310 receives a first quantity of vapour evaporated from the outer surface of the condenser tube 1220 (typically at the desired flow rate e.g. 2 kg/hr) having an inlet 1222 and a second volume of vapour which is allowed to exit past the functional end of the condenser tube 1220 and be re-circulated back to the compressor inlet 1310. The volume of excess vapour thus recirculated can be in 100 to 500% of desired flow rate, preferably 250%. The compressor 1300 delivers the compressed vapour to the condenser tube inlet 1222 through compressor outlet 1320. This large recirculating volume of vapour is released at the end of the condensing tube 1220, through one or more nozzles 1230 (see FIGS. 3 and 4) which reduces the pressure to ambient, and the vapour is therefore at saturation temperature. This is quite distinct from the very small volume allowed to escape at the start of the heat exchanger tube 1120, when still superheated, through an opening 1152 in vertical tube 1150. The only purpose of the gas thus injected is for degassing rather than thermal management, as the vapour thus injected is carried outside the system 1000 via the gas outlet 1170. Thus, the vertical tube 1150 extending into chamber 1130 need not be provided and may be substituted by e.g. an elongate vapour injection nozzle for the purpose of degassing. The inventor has discovered, however, that by extending the tube 1150 into the degassing chamber 1130, the superheated vapour inside the tube 1150 will maintain the tube wall at a temperature higher than 100 C (e.g. up to 120 C) causing heat transfer to the fluid in chamber 1130, usefully adding heat energy to the fluid in chamber 1130, thus saving energy by reducing the power input requirement of heater 1140. The heater 1140 may be an electric heater.

Figure 3:
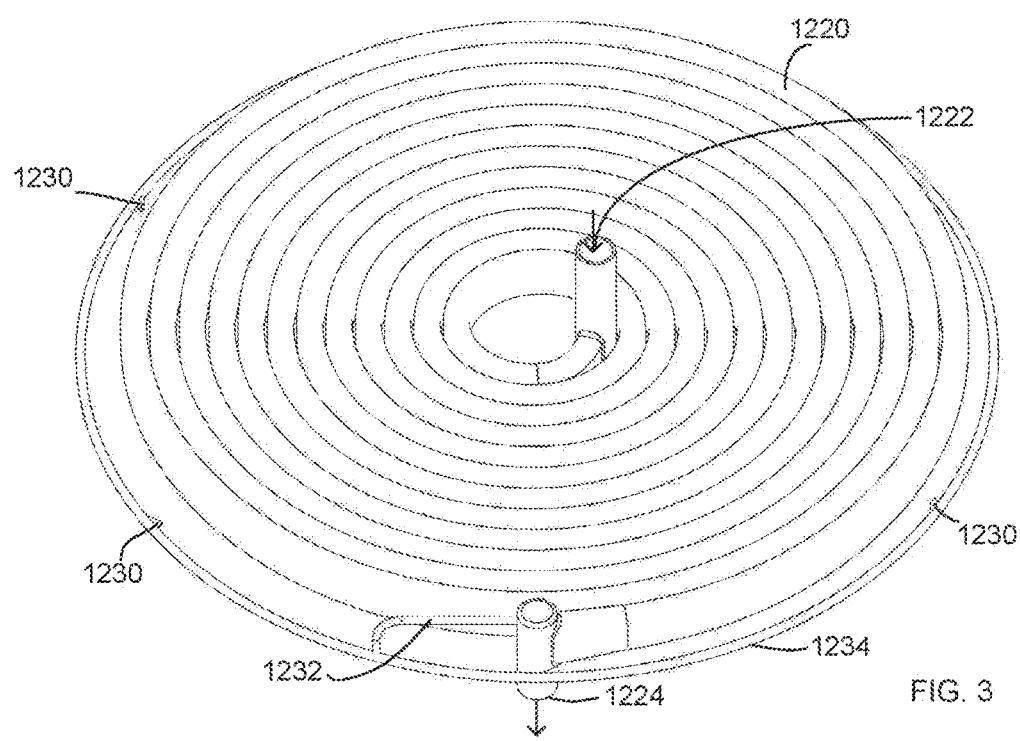
FIG. 3 is an isometric view showing a spirally coiled condenser tube of an evaporator-condenser module according to an embodiment of the invention.
Figure 4:
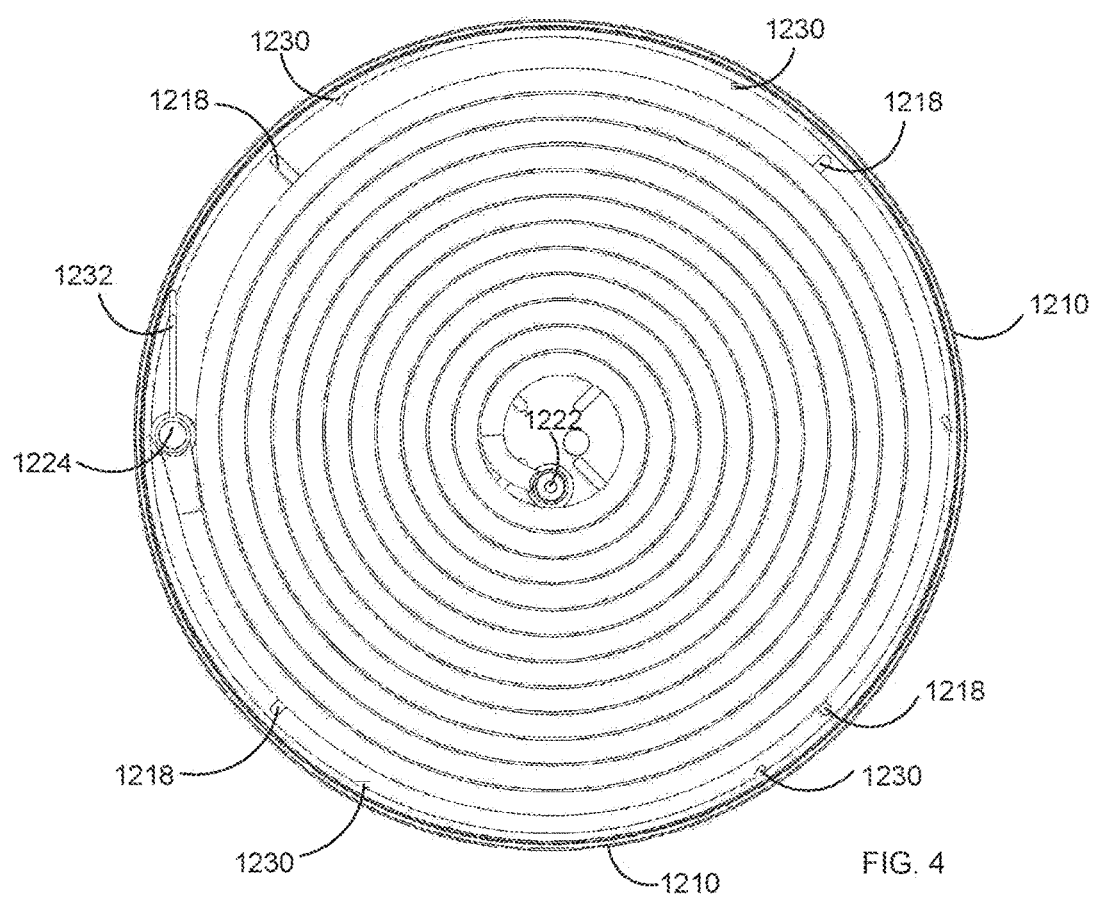
FIG. 4 is a plan view showing the condenser tube of FIG. 3, inside the lower housing of the evaporator-condenser module.

In a preferred embodiment, one or more nozzles 1230 in fluid communication with the compressor outlet 1320 via the condenser tube 1220 are provided in the lower housing 1210. These are illustrated in FIGS. 3 and 4. Ideally, the nozzles 1230 are spaced around the inside periphery of the lower housing 1210 and inject pressurised vapour into fluid in the housing 1210 to increase wetting of the outside of the condenser tube 1220. The flow path through the connection from the condenser tube 1220 to the nozzles 1230, and indeed the nozzles 1230 themselves will provide a certain flow restriction to the flow of vapour therethrough. This resistance to flow is designed to restrict flow to approximately 250% of system design flowrate (e.g. for a system design of 2 kg/hr, this system will allow 3 kg/hr to flow through the nozzles 1230 at a pressure drop of 0.2 bar). Preferably the nozzles 1230 are situated below the fluid level in the housing and during operation, will have the effect of producing a circular fluid flow pattern. This causes the fluid to be drawn along the condenser tube spiral 1220 towards the centre of the housing 1210. The exit velocity will result in water droplets breaking free of the surface and splashing/wetting the condenser coil 1220. The nozzles 1230 may be supplied with vapour from a ring 1234 connected by a pipe 1232 to the condenser tube outlet 1224, or any similar interconnecting means. A number of radial channels 1218 in the housing base 1210 encourage fluid to return from the centre of the housing 1210 toward the outer portions of the housing.

The inlet 1310 to the compressor 1300 draws in all the recirculated vapour (as discussed above) and the evaporated vapour. It is preferred that no water droplets, or mist are carried into the compressor 1300, as such droplets would carry contamination. The compressor supply 1310 is therefore mounted in an elevated plenum, distant from the surface of the water. The area of this chamber is arranged such that the vertical flow velocity is not sufficient to entrain mist or droplets which will therefore return to the liquid region under gravity. This area can also be arranged to receive a mist eliminator as is known to persons of skill in the art.

In preferred embodiments, the evaporator-condenser module 1200 has a fluid level control means to monitor the level of fluid within the housing 1210 to optimise wetting of the outer surface of the condenser tube 1220. It is preferred, however, that a fluid level sensor is not located within the housing 1210 per se. This avoids problems arising from a fluid level sensor within the housing 1210 trying to detect the level of a bubbling fluid surface and the sensor becoming compromised due to dissolved solids precipitating out of the fluid and coating the sensor. Thus, the level of fluid within the housing 1210 is determined by reference to a fluid level sensor 1460 in an evaporator level sensing chamber 1400 as shown in FIG. 5. This evaporator level sensing chamber 1400 provides the function of level control of fluid in evaporator-condenser module 1200, without any direct contact with that fluid and additionally provides an exit route for the gases removed. This combination of functions helps reduce the number of components and therefore complexity and cost. Critically in a sterile sensitive application, it allows the evaporator-condenser module 1200 to be designed with only simple vertical openings and no re-entrant features. This reduces the risk of organic compounds collecting, and therefore reduces the risk of biofilm growth.

Vapour collected in the evaporator-condenser module 1200 rises to the ceiling of upper housing 1212 and flows from evaporator-condenser module 1200 into the compressor 1300 through compressor inlet 1310. The compressor 1300 delivers pressurised vapour at a compression ratio of at least 1.1, preferably 1.15, more preferably 1.2 or 1.4 or more, through outlet 1320 into condenser tube 1220 via opening 1154. A compression ratio of 1.2 will provide a saturated steam temperature of 105 C within the condenser tube 1220.

The condenser tube 1220 is arranged such that the liquid/vapour inside the tube 1220 is at the saturation temperature of the compressed vapour, typically 105 C for 1.2 bar and the liquid/vapour outside of the tube 1220 is at the saturation temperature of uncompressed vapour (100 C for water). The 5 k temperature difference across the tube wall will result in the desired transfer of heat being achieved. By way of example, for a desired condensate mass flowrate of 2 kg/hr, the evaporator-condenser module 1200 will need to condense 47.62 L/min of steam. A compressor 1300 designed for a flowrate of 119 L/min will provide the excess velocity required to keep the inside of the condenser tube 1220 substantially clear of droplets. This high velocity can help reduce the collection of pools of condensate, and thus maintain a thin film of condensate on the condensing tube 1220 inner surface. As water is a poor thermal conductor, a thinner layer is better. Using this method helps to maintain a heat transfer coefficient in the region of 8000 W/m$^2$k from steam to tube inner wall. The evaporating fluid on the outside of the tube 1200 cannot benefit from the high velocity stream, and some will be immersed in water, but, due to the agitation and circulation discussed (e.g. from steam nozzles 1230) a heat transfer coefficient of 5860 W/m$^2$k can be achieved from tube 1220 outer surface to evaporator fluid and using a copper condenser tube 1220, a calculated overall heat transfer coefficient of 2800-3200 W/m$^2$k may be achieved. (The overall heat transfer coefficient for a stainless steel (SS) tube is about 10% less than when using a copper tube). A 9.52 mm diameter tube with a length of 4.2 m can therefore provide the required surface area to achieve a 2 kg/hr evaporation and condensation flow rate.

Water droplets form on the inside surface of the condenser tube 1220. If left to collect in the tube 1220, the droplets will prevent vapour from coming into contact with the inside wall of the tube 1220 thus reducing heat transfer. To mitigate this, the velocity and volume of the vapour travelling in the tube 1220 is increased by providing a vapour exit means at the end of the condenser tube 1220 and allowing a volume to recirculate to the compressor inlet 1310, which continually circulates more vapour through the condenser tube 1220 than is required to maintain a target condensation rate. For example, if a target purified water output is 2 kg/hr, a volume of 5 kg steam is circulated. By maintaining a steam velocity in the condenser tube 1220 of approximately 100 m/s, even small droplets of condensate can be swept to the condensing tube outlet 1224 (see FIGS. 3 and 4) optimising the available dry surface area for further condensation. Preferably, the condenser tube 1220 is a single continuous tube avoiding problems arising from joints and seals including leakage, contamination and efficiency losses.

The condenser tube outlet 1224 delivers high volumes of high velocity vapour and much smaller flow rates of condensate. For the water example above, typically the output is 85 L/min of steam and 0.033 L/min of water. These flows are separated by a simple separator formed by the arrangement at the end of the condenser tube 1220 as illustrated in FIG. 3. The separator includes a horizontal inlet conduit, an upward steam conduit and a downward condensate conduit. The mixed flow enters the separator via the horizontal inlet conduit and must turn abruptly through e.g. 90 degrees as shown in FIG. 3. The high velocity steam turns and enters the upward steam conduit for recirculation to the compressor 1300. The inertia of any condensate droplets in the horizontal conduit causes them to contact an endwall of the separator, and flow under gravity through the downward condensate conduit to the condenser tube outlet 1224 with a gas flow velocity therethrough of effectively zero. This arrangement of providing a spiral condenser 1220 tube permits all sections of the tube 1220 to be equally immersed on a single level pool of fluid for evaporation. Traditionally the condenser tube is arranged as a bundle of parallel tubes at different vertical levels requiring the fluid for evaporation to be pumped and carefully distributed to flow evenly over all the tubes in the bundle (known as a falling curtain evaporator). Other methods of achieving a thin film require the condensing tube 1220 to be constructed in thermal contact with a flat plate, and a system of mechanical wipers constantly wipe excess water from the evaporating surface to provide a consistent thin film. Both these and other known methods are significantly more complex to implement, and require additional functional components (pumps/wipers etc.)

In forming the spiral tube 1220, it is advantageous to slightly flatten the tube 1220. This novel arrangement provides the advantage of maintaining the desired outer surface area, while reducing the cross section. The reduced cross section in turn reduces the volume of vapour needed to achieve the same velocity. It also permits the entire spiral tube 1220 to fit into a smaller outer diameter (in plan view, as shown in FIGS. 3 and 4).

Figure 8:
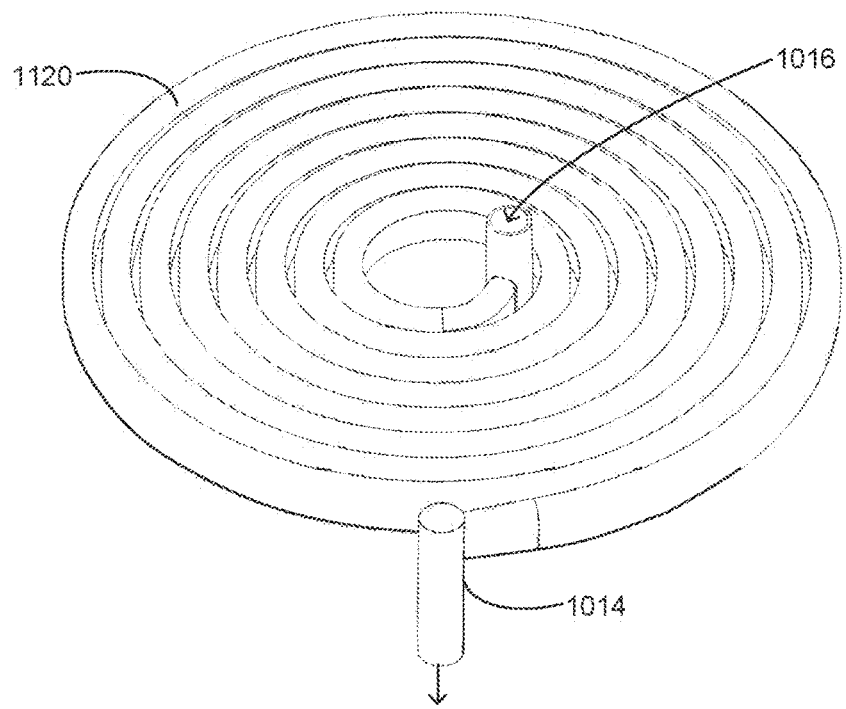
FIG. 8 is an isometric view showing a spirally coiled heat exchange tube of a heat exchanger module according to an embodiment of the invention.
Figure 9:
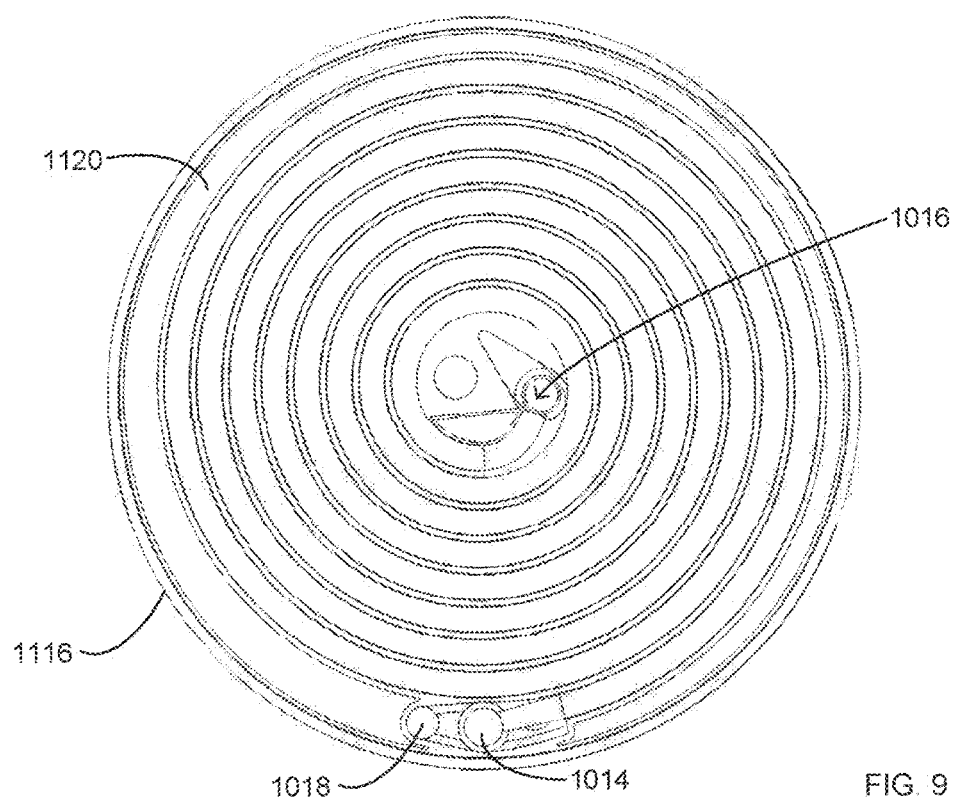
FIG. 9 is a plan view showing the heat exchange tube of FIG. 8, inside the lower housing of the heat exchanger module.

Condensate exiting the separator through condenser tube outlet 1224 will be at saturation temperature (105 C for 1.2 bar pressure). Therefore, it is desirable to cool the condensate to close to ambient temperature before collection for use or delivery to a patient. Thus, the condensate is passed through the inside of thermally conductive tube 1120 in the heat exchanger 1100 returning heat in the condensate to fluid covering the tube 1120 in the heat exchanger housing 1100. As shown in FIGS. 3 and 4, the condensate exits the condenser tube outlet 1224 and enters the condensate inlet 1016 (see FIGS. 8 and 9), which is in fluid communication with the heat exchange tube 1120. Ideally, the conductive tube 1120 has a length to diameter ratio of more than 50, preferably between 200 and 600 and more preferably, between 350 and 450.

For compliance with medical device standards, such as when the purified fluid produced by system 1000 is used for preparation of treatment fluids (e.g. dialysis, IV fluids), it is advantageous to be able to inspect the internal working surfaces of the system 1000 which are subject to scale buildup or corrosion. Conventional heat exchanges such as shell and tube, tube in tube or plate exchangers, do not lend themselves to this requirement. This is particularly the case when a single, substantially downward depending, self-draining process flow is desired, which is substantially free of re-entrant features. The inventor has advantageously devised a system and method to address these problems as will now be described.

Preferably, the incoming cold water or fluid flow from heat exchanger inlet 1018 (see FIG. 9) is confined in the heat exchanger module 1100 such that it flows in a channel 1118 substantially coaxial with, and closely confined to the outside of the tube 1120 containing the condensate, but flowing in the opposite direction. To maintain dimensional control of the tube 1120 relative to adjacent close tube walls, small locating/spacing ribs can be provided at intervals along the length of the tube 1120. These can be separate components, or preferably formed as either part of the tube 1120 or channel 1118. Advantageously, the channel 1118 may be formed without an additional conduit but instead as part of the overall construction of the heat exchanger module 1100 whereby the channel 1118 occupies the void between the module's upper housing 1112 having spiral groove 1105 and the coiled tube 1120 and lower housing 1110 (see FIGS. 1 and 7) which may be moulded or machined to accommodate the spirally coiled tube 1120. Whereas counterflow "tube in tube" heat exchangers are known, and are very efficient, a common problem when heating raw water is that scale and solids in the incoming water will separate out, and no means is provided to easily mechanically clean it. The inventive arrangement disclosed herein provides an outer tube that can be opened allowing both inner and outer surfaces of the raw water channel 1118 to be easily accessed for cleaning, while maintaining a flow channel 1118 with a small cross-sectional area. The small cross section of the channel 1118 is important to increase flow velocity. This in turn is needed (a) to entrap gas bubbles as they come out of solution and carry them to the exit and (b) provide the higher velocity that improves the heat transfer coefficient. In forming a conventional tube in tube heat exchanger, or a plate heat exchanger, the very small clearances as required for this system (e.g. 0.25 mm) would be impossible to achieve.

Using this arrangement, an internal heat transfer coefficient from condensate to tube wall in the region of 1800 $W/m^2k$ may be achieved, and an external coefficient of 1600 $W/m^2k$ from external tube wall to the incoming water or fluid. A standard 9.52 mm copper tube 1120 with a wall thickness of 0.71 mm is estimated to result in an overall heat transfer coefficient of 781 $W/m^2k$. (A thinwall 10 mm SS tube would have a slightly higher value of 784 $W/m^2k$). For the example provided herein seeking a purified water flow of 2 L/hr a LMTD (logarithmic average of the temperature difference) of between 5K and 3.5K may be achieved. Thus, if the condensate had an initial temperature of 103.5 C when entering tube 1120, and the inlet cold water a temperature of 20 C, then the condensate will discharge at 23.5 C and the incoming flow will be heated to 100 C providing an energy recovery efficiency of greater than 95%.

As water evaporates, only pure vapour leaves the surface as steam, and the concentration of solids in the remaining fluid therefore increases. This can ultimately lead to a build-up of solids and sludge that can compromise operation of the system 1000. Thus, a bleedoff outlet 1274 (see FIG. 5) is provided to place an upper limit on the degree of concentration of solids or sludge in the evaporator-condenser housing 1210. Preferably, the bleedoff outlet 1274 is provided distally of the incoming fluid flow where concentration of solids is likely to be highest. By providing agitation means (ring of vapour nozzles 1230) the distribution in the chamber 1240 will be uniform, and the bleedoff outlet 1274 can be located anywhere. Preferably, the flow rate through the bleedoff outlet 1274 is adjustable and is typically in a range of 1% to 15% of the inlet flow rate. Typically the bleed off flow rate would be determined according to local conditions, where the flow rate would be higher where unprocessed fluid sources contain higher levels of impurities. This enables the concentration of impurities in the system 1000 to be limited by dilution, as the more concentrated working fluid achieves a set outlet flow rate, which will automatically be matched by an increase in the inlet flow rate (via level sensor 1460) to make up for the bleedoff.

In a preferred embodiment, heat energy is recovered from the bleedoff fluid by passing it through a secondary flow channel 1180 in the heat exchanger module 1100 as shown in FIG. 1. While the secondary flow channel 1180 is illustrated as parallel with the vertical axis of tube 1120, it is to be understood that other arrangements are possible, e.g. with secondary flow channel 1180 being arranged parallel and concentrically with part or all of tube 1120. Ideally, the cold fluid channel 1118 is configured to enclose both the conductive tube 1120 and secondary channel 1180 as shown in FIG. 7, thus surrounding them with a flow of infeed water. In this manner the combined flow of condensate and bleedoff will more exactly match the inlet flowrate, and provide an efficient heat exchanger.

The bleedoff rate could be set at a relatively high value to ensure low concentration of solids in the system 1000. However in areas with very low Total Dissolved Solids (TDS), this will result in waste of energy and reduction in performance. When the inlet water is of good quality with low TDS, a bleedoff rate of the order of 1% may be sufficient. In areas with very hard or brackish water a bleedoff rate of 15% or higher may be required. The inlet to the bleedoff pipe 1270 is submerged in fluid in the evaporator-condenser module 1200 in a suitable area of the contaminate concentration (e.g. distally of the incoming fluid flow). The water level in this area is controlled by evaporator fluid sensing means 1460 to be substantially constant during normal operation. The flowrate discharging from the outlet 1274 of the bleedoff pipe 1270 is therefore controlled by the height of the bleedoff outlet opening 1274 with respect to the fluid level in the evaporator-condenser module 1200. The potential head pressure will be countered by the system resistance, k, and the water velocity establishing a relatively fixed flowrate for a given height difference. Thus, in a preferred embodiment the bleedoff outlet opening 1274 is flexibly mounted so that its height can be adjusted, in turn adjusting the bleedoff flow rate. A scale or guide may be provided on the bleedoff outlet 1274 allowing the user to select the height setting according to e.g. desired bleedoff rate as a fixed percentage of incoming flow, for example from 1 to 15%. Alternatively, the scale could be calibrated to indicate local water condition, so that the user simply selects a value or marking corresponding to e.g. local water hardness or TDS value. The outlet 1274 can also be provided with a flow control means such as a non-return valve to prevent reverse flow.

The compressor 1300 is configured to provide a pressure ratio of at least 1.1, preferably 1.15, more preferably 1.2 or 1.4 or more. This pressure is provided to elevate the saturation temperature of vapour (e.g. from 100 to 103.5-105 C or higher) so that the condensing temperature (high pressure side) will be higher than the evaporating temperature (inlet side) thus facilitating "free evaporation" of the fluid. The compressor design, in addition to the pressure discussed above will have a specified flow rate. This is designed to be about 250% to 300% of nominal system requirement so that heat transfer on the inside of tube 1220 of the evaporator-condenser module 1200 can be maximised by keeping it clear of condensate build up. When analysis of inlet water indicates a bleedoff rate of significantly more than 15%, pre-treatment of the inlet water can be employed to maintain optimum performance, for example by the use of known methods such as particulate filters, reverse osmosis technology or water softener methods as appropriate for local conditions.

The compressor 1300 may take any suitable form capable of achieving the required increase in vapour pressure while meeting target energy and size constraints that enable the system 1000 to meet running efficiency, size and other performance objectives. An important requirement for certain medical applications is that there should be no risk of contamination—for example lubricating oil or wear of compressor components. This means that vane, screw and reciprocating compressors are not desirable. Furthermore, diaphragm or peristaltic pumps are unlikely to satisfy the size constraints. A preferred embodiment of the system 1000 as a whole is intended to be portable and operable from non-mains power such as from solar, wind or a battery. It is known to make Vapour Compression distillers for large installations with water flowrates of many tons of water per hour. There are even examples in the prior art which refer to "small systems" in terms of 4 kW power input. The inventor has sought a system and method to provide for an energy input which is an order of magnitude lower again. The overall energy consumption of system 1000 is ideally limited to a maximum of 500W, preferably 300W and more preferably still, 150W to 200W. In some systems, the available power supply may be as low as 75W to 150W and some embodiments of the fluid purification system are configurable to operate within such power constraints.

The low power supply requirement rules out diaphragm-type compressors because of the losses that occur during operation. Similarly, reciprocating positive displacement compressors are known but not available or known to be suitable for small scale use in vapour compression (since steam would result in corrosion); these devices are typically suitable for higher pressure ratios and lower flow rates.

Figure 6:
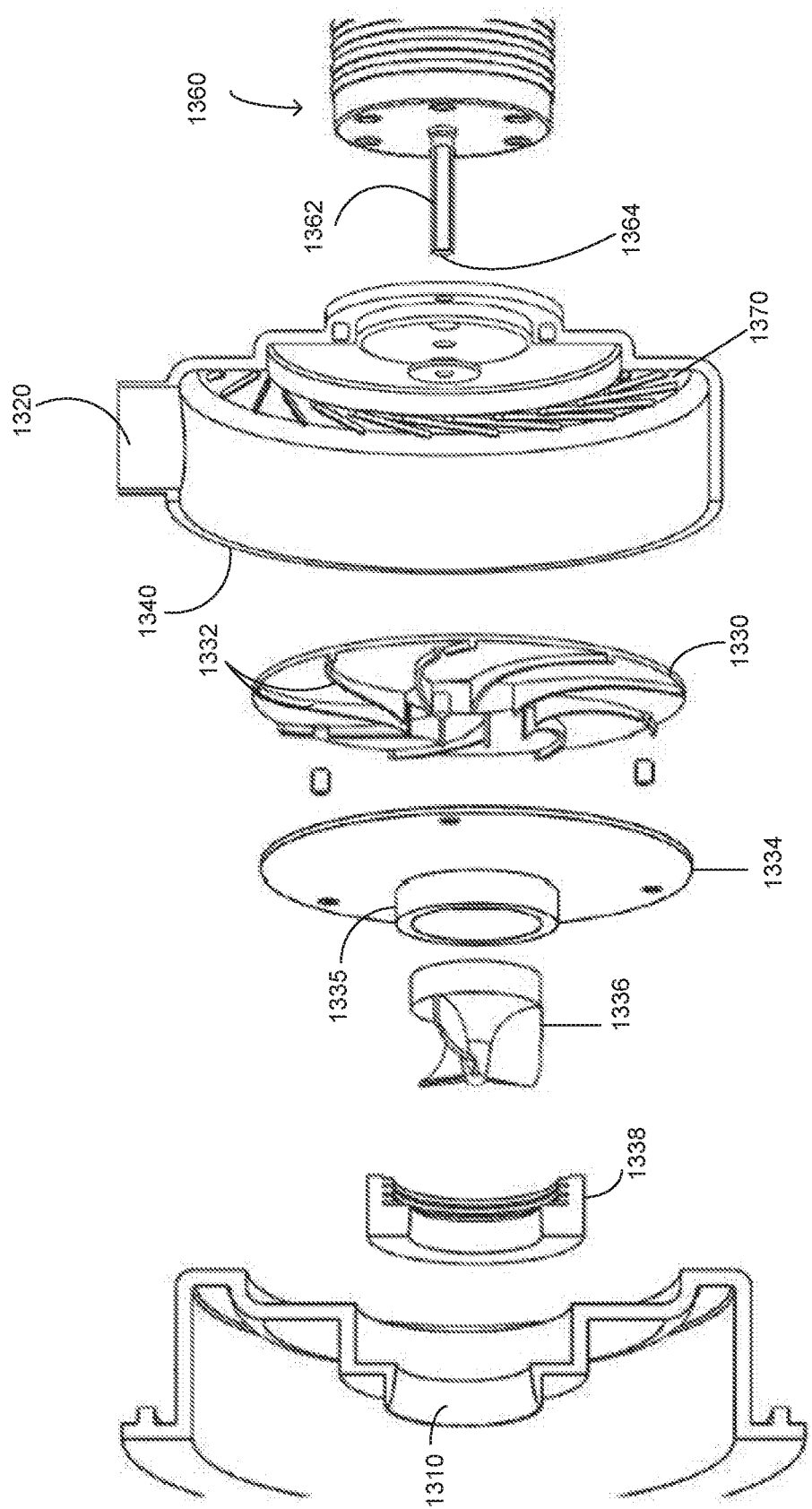
FIG. 6 is an exploded isometric view of components of a micro compressor according to an embodiment of the invention.

FIG. 6 is an exploded isometric view of components of a micro compressor 1300 according to an embodiment of the invention. The compressor 1300 has an impellor 1330, having radial vanes 1332 of less than 2 mm radial height, preferably less than 1.7 mm radial height based on an impeller diameter of in the range of 40 to 60 mm, and preferably about 50 mm. A separately manufactured shroud 1334 is fixed to the impellor 1330 by e.g. riveting, bonding brazing and/or welding. An inlet inducer 1336 of the compressor 1300 can also be configured as an alternative means of fixing the shroud 1334. A threaded coupling between a motor shaft 1362 of the compressor 1300 and the inducer 1336 can in turn urge the shroud 1334 into contact with the impeller 1330, and the rear of the impeller 1330 in turn can be arranged to slide onto the shaft 1362, but have its axial movement arrested by a shoulder on the shaft 1362. The union of the shroud 1334 and impeller 1330 form a number of substantially circumferentially enclosed pockets of vapour between each vane 1332 during operation, mitigating vapour flow losses across the vane walls.

It is known to attach an impellor to a drive shaft, typically using discrete components such as a collet and associated clamping means. At the micro level envisaged, it is not possible to fabricate these components. An alternative means relies on an interference fit, where the interference is represented as a percentage of the shaft diameter. Again, at the small scale envisaged, this design would require tolerances that are not industrially achievable. The inventor has therefore proposed a steam compressor 1300 with a steam flowrate of less than 250 L/min, which can be manufactured using current production means as will now be described.

In some embodiments, compressor 1300 includes a separately manufactured inducer 1336 formed of elastomeric or compliant material. The inducer 1336 has a plurality of inducer vanes at one end and blind bore in the opposing end which is configured to receive the shaft 1362 of motor 1360 as shown in FIG. 6. The compliant nature of the inducer 1336 enables the shaft tip 1364 to become engaged in the inducer bore without the need for fasteners such as nuts and bolts (as used in traditional compressor assemblies) giving rise to reduced complexity, size and weight in the inventive micro compressor 1300. Additionally, the compliant nature of the inducer 1336 provides noise attenuation benefits. An alternative arrangement could provide the inducer 1336 with a rigid threaded insert for coupling with the motor shaft 1362. A further alternative could provide an inducer 1336 of substantially rigid material but with slender vanes to provide some compliance between the inner shaft mounting axis and a circumferentially distal axis surface of commensurate diameter to the shroud inlet, acting in turn as an extension 1335 and providing the force necessary to lock the shroud 1334 to the impeller 1330.

In some embodiments, the compressor 1300 includes an outlet diffuser 1370 as shown in FIG. 6. The diffuser 1370 is positioned downstream of the impeller 1330 in the flow path and converts high velocity gas entering through the inlet 1310 into pressure by gradually slowing (diffusing) the gas velocity. The diffuser 1370 includes a plurality of vanes which discharges the diffused gas into an outlet volute of the collector 1340 for exiting through outlet 1320. Alternatively, the diffuser 1370 can be vaneless, vaned or an alternating combination and shaped as a wedge, channel or pipe as is known to a person skilled in the art. The vaned diffuser 1370 can also have a wide range of solidities for high efficiency operation of micro compressor 1300. Preferably, the alternative arrangement has the advantage of permitting disassembly and reassembly by a non-specialist operator.

Further reduction in losses between the impellor 1330 and collector 1340 can be achieved by reducing the gap 1380 (see FIGS. 1 and 2) between the two components from e.g. 0.5mm as is typical in known centrifugal compressor devices, to 0.25mm or less thereby limiting flow losses escaping through the gap 1380 between the impeller 1330 and the collector 1340 and returning to the inlet 1310. However, this is difficult to achieve given the small size of the micro compressor 1300 and available manufacturing tolerances. Advantageously, the inventor has mitigated this loss by extending shroud 1334 to extend axially at collar 1335 providing a substantially cylindrical area of smaller diameter in the order of 25% of the diameter of the shroud 1334 (e.g. 10 mm diameter for the collar 1335 compared to 40 mm diameter for the shroud). This in cooperation with seal 1338 reduces the gap 1380 through which escaped vapour may return to the inlet 1310 to the order of 0.1 mm. To illustrate, the area permitting leakage around the impellor 1330 may be of the order of $\pi \times 0.3$ mm$\times 50$ mm=approximately 50 mm$^2$. However, at the shroud 1334 as proposed this would reduce to $\pi \times 0.1$mm$\times 15$ mm=1.5 mm$^2$ thus reducing flow losses by more than 80%.

Alternatively/additionally, a front seal 1338 may be provided to limit flow of escaped vapour back into the inlet 1310. In fact, a number of seals may be incorporated in the micro compressor assembly to mitigate flow leakage. Seals formed from an elastomeric material such as silicon-rubber also have the benefit of attenuating sound pressure waves and high frequency vibrations from the compressor 1300 limiting noise breakout from the compressor 1300 during operation. Further noise attenuation may be achieved by constructing the outlet collector 1340 from a single piece of material which directs the compressor outlet flow through at least two turns of approximately 90 degrees before exiting the compressor body through outlet 1320. Each turn serves to reflect back some of the sound waves, thus reducing the amplitude of sound pressure waves exiting the system 1000.

Referring again to the "stacked" arrangement of the components of the fluid purification system 1000, the inlet and outlet conduits 1310, 1320 are preferably arranged so as to additionally perform the function of a direct mounting means for the compressor 1300 on the top surface of the top housing 1212 of the evaporator-condenser module 1200. Omitting dedicated mounting brackets and footings reduces complexity as well as size, cost and weight contributing to the low cost and weight of the system 1000. Ideally the inlet and outlet conduits 1310, 1320 are sufficiently rigid to support the compressor 1300 yet also resilient enough to prevent the transmission of high frequency vibrations to the evaporator-condenser module 1200. In the embodiments illustrated, the compressor 1300 includes a horizontal axial orientation with respect to the motor 1360. It may be preferable however, for the compressor 1300 to include a vertical axis orientation in which the motor 1360 is at the greatest height of the stacked configuration of system 1000 (not shown). Ideally, the power supply cable (not shown) is coupled with the compressor 1300 distally of the inlet and outlet conduits 1310, 1320 and has sufficient free length that in normal operation, it is slack to avoid transmission of vibration but can become tautened when movement approaches safe limits such as during transport thus preventing further movement.

FIG. 7 illustrates in greater detail features of the heat exchanger module 1100 according to an embodiment of the invention, facilitating degassing. The bulk fluid in the degas chamber 1130 will be "degassed", as further fluid enters from the heat exchanger outlet it will mix with this fluid. Gas bubbles arriving with the flow will rise vertically towards the gas outlet 1170. Gas entrained or saturated in this fluid will be stripped or substituted by the combined effect of the steam bubbles and further heating taking place in the degas chamber 1130 (both from the vertical tube 1154 carrying superheated vapour if present and the electric heater 1140) such further heating causing the fluid to boil. Partially heated fluid from channel 1118 and partially degassed fluid from the heat exchange tube 1120 is collected in chamber 1130 and chamber column 1132. Pressurised vapour from compressor 1300 is injected into chamber column 1132 via opening 1152 shown here in the form of a nozzle, to produce a stream of gas bubbles in the fluid to be degassed. A wall 1134 separates chamber 1130 from a degassed fluid outlet chamber having outlet 1172. A slot 1136 in wall 1134 allows degassed water to flow into the degassed fluid outlet chamber and through outlet 1172 to the evaporator-condenser module 1200. Gas separated from the fluid in chamber 1130 rises to the top of the chamber 1130, which ideally has sloping surfaces arranged so that rising gas and bubbles are directed to the gas outlet 1170 after which it ultimately exits the system 1000 through the chamber 1400 and mixes with atmospheric gas, ideally through a gas catchment apparatus. A non-return valve mechanism can be provided to prevent inflow of atmospheric gas. It should be noted that the gas and water level outlet 1170 is disposed towards the top of the chamber 1130, whereas the degassed fluid flow outlet 1172 has its inlet disposed towards the bottom of the chamber 1130 as shown in FIG. 7. Thus is provided a degas chamber 1130 formed as an integral part of the heat exchanger module 1100, where both the degas chamber 1130 and heat exchanger module 1100 share the components of the lower and upper housings 1110, 1112, thus reducing system cost and complexity. This arrangement has not be achieved or contemplated by existing prior art systems.

Ideally, gas outlet 1170 is in communication with an elongate tube 1420 forming part of the evaporator level sensing chamber 1400 as shown in FIG. 5. A first end opening 1422 of the tube 1420 is in fluid communication with the chamber 1130, and a second end opening 1424 of the tube is exposed to atmosphere. A third opening 1426 is provided intermediate to the first and second ends, which is also exposed to atmosphere. A temperature sensor 1190 is provided within the elongate tube 1420 at a location between the third and second openings 1426, 1424. This arrangement provides for control of the exiting rate of gas and steam. It will be appreciated that if an excess of steam is flowing through the first opening 1422, it will exit both from the second and third opening 1424, 1426, thus ensuring that the temperature of the sensor 1190 is close to 100 C. If the exiting steam flow is very low, then natural circulation between the third and second openings 1426, 1424 will maintain the sensor 1190 at a temperature close to ambient for example 20-30 C. Additionally, level sensor 1460 in the chamber 1400 detects the level of fluid in the condenser-evaporator module 1200 for use in flow control at the inlet as described elsewhere herein.

Temperature sensed by sensor 1190 located at the gas outlet 1424 of the system 1000 can be indicative of steam outflow velocities which are in turn indicative of the naturally induced flows or ambient air drafts present in the region between the second and third openings 1424, 1426, and can exhibit a temperature change from ambient to close to boiling point as the velocity of gas and steam at the outlet 1424 is marginally increased.

Since the overall system 1000 is substantially gastight with the exception of the second and third openings 1424, 1426 at the temperature sensor 1190, the inflow of fluid at the heat exchanger inlet 1018 (see FIG. 9), although at a distal part of the system 1000, when combined with the energy input via the heater 1140 and compressor motor 1360, will give rise to gas outflow at the temperature sensor 1190. Therefore, measuring the temperature at sensor 1190 can be used as feedback for a control system with a set point targeting a nominal steam and gas outflow. This outflow is achieved by modulating the power delivered to heater 1140. This method has the advantage of automatically compensating for any variations in the evaporation or condensation rate which may occur, and also preventing the ingress of external air by maintaining a positive flow of steam and gas in the outward direction.

The micro distiller system 1000 operates at very low flow rates. The flow for a common tap flowing at a rate of about 2 L/hr would be observed as a series of droplets rather than a constant flow stream. It becomes a difficult challenge to retain precise control over such a minute inlet flowrate, especially when considering that an "error" of even 1% will result in system failure. By adjusting steam flow in a manner which maintains the temperature of the sensor 1190 even in a wide region of 60-80 C, the inventor has devised a means of using a relatively low cost, imprecise temperature sensor to maintain a delicate steam/gas outflow of in the region of 0.0 to 0.25 m/s at outlet 1426. This relatively imprecise measure in turn provides a very precise means to control a parameter that is otherwise very difficult to predict or measure, i.e. the optimal cold fluid inflow rate. This arrangement and method has not be achieved or contemplated by existing prior art systems.

Vapour and condensate flow out from condenser tube 1220 are pressurised hence in preferred embodiments, one or more flow restrictors are provided to manage the flow such that a desired flow rate of e.g. 100 L/min to 150 L/min can be achieved with a pressure drop that is commensurate with the compressor discharge pressure (e.g. 0.2 bar). The exiting velocity from the restrictor or restrictors can be usefully employed in agitating the water in the evaporator-condenser chamber 1240 to further enhance the thin film covering of the condenser tube 1220 described above.

The condensate flow could similarly be controlled by providing a restricting orifice with a pressure drop matching the compressor pressure at the design flowrate. The area immediately downstream from the orifice would have a pressure of 1 bar but a water temperature of 105 C resulting in the superheated water flashing to steam. The increased volume could potentially result in abrupt ejection of condensate from the heat exchanger module 1100. The inventor has realised that if the restrictor, in the form of a controllable valve is placed at the outlet from the heat exchanger module 1100, this problem is avoided. This also provides the benefit of being able to recover the thermal energy, as the incoming condensate at 105 C can be cooled to within 3.5 to 5K of ambient temperature before the pressure is lowered to ambient pressure. This controlling valve could be set to a fixed orifice size. However, it is preferable that the valve is adjustable to maintain a fixed level of condensate such that the condenser tube 1220 is always drained of condensate but the heat exchanger 1100 is always flooded during operation.

Thus, in a preferred embodiment a condensate level sensing chamber 1500 is provided between the condenser outlet 1224 and the heat exchanger condensate inlet 1016 as shown in FIG. 5. A fluid level sensor 1560 is sensitive to the condensate level in chamber 1500. A system controller receives feedback from fluid level sensor 1560 and adjusts a heat exchanger condensate outlet valve 1012 to maintain a fixed condensate level in said chamber 1500.

In a preferred embodiment, the degassing chamber 1130 (including the gas outlet 1170 and degassed water outlet tube 1172), a portion of the heat exchanger 1100 and a portion of the evaporator-condenser module 1200 are integrally moulded such that they share common housing components, namely upper and lower housing portions. Advantageously, this enables the number of components in the fluid purification system 1000 to be reduced. This reduces the expense of the system 1000 and further due to the modularity of the components, provides for ease of cleaning of the component surfaces.

Advantageously, the inventive system 1000 is configured in such a way that it is free draining and easily sterilised. This is exemplified in a start-up procedure in which the system 1000 is sterilised and purged before use in the production of sterile fluid. This sterilising process can only function when the condensate that collects initially as the system components are heated by the steam generated by the heater 1140 can drain freely either back towards the heater chamber 1130, or towards the outlet 1170, from compressor 1300, through condenser tube 1220, condenser fluid level area and the condensate valve 1012 (see FIG. 5). This is important for sterilisation. Advantageously, the present invention provides reliable sterilisation due to the fact that the condensed fluid flows in a single contiguous tube. If two or more tubes were used in parallel, as is common in shell and tube heat exchangers, a delivery of sterilizing steam can pass through some tubes, but not others leading to a dangerous situation of pockets of unsterilised surfaces.

The inventive fluid purification system 1000 is advantageously disposed with all connections between modular components disposed vertically so there is minimal leakage due to gravitational filling and disassembly of the component parts is made easy, e.g. for cleaning, maintenance and the like. Furthermore, the physical arrangement of each component in certain embodiments optimises thermal efficiency between "heating" and "cooling" features of the system 1000 so that purified condensate produced by the system 1000 is only a few degrees warmer than cool unpurified fluid entering the system 1000.

The inventor has recognised that common micro centrifugal compressors are a very uneconomical proposal for devices requiring very small flow volumes, such as for preparing WFI for patient use. The losses due to clearances between the impellor and housing of the compressor have an increasingly disproportionate effect with regard to enthalpy. This is particularly illustrated in FIG. 10, which shows a prior art enthalpy-entropy chart comparing the performance of a large efficient compressor and a small inefficient compressor utilising water as the compressor fluid. The bold curved line shows the typical performance of a large commercial efficient compressor; the dotted curved line shows the typical performance of a small inefficient compressor. When the dotted curved line becomes tangential to the solid line (p=1.2 bar), no further pressure increase occurs with increasing revolutions per minute (rpm) of the compressor—instead there is more heat generation. The effect is that the enthalpy increases disproportionately. This may occur at 1.15 bar or even as low as 1.1 bar—hence, it is desirable to reduce losses/leakage at the compressor. For best efficiency, a micro compressor of the present system 1000 would be more efficient at 20 mm dia and 200,000 rpm instead of 50 mm dia at 80,000 rpm. However, this extreme rpm is not practical and thus the inventive system 1000 is directed to reducing losses/leakage of the compressor.

In order to provide an efficient system 1000, the inventor has designed the compressor 1300 to reduce the dynamic losses in three areas: (a) across the vane walls, by providing an inventive means of shrouding the compressor vanes; (b) leakage from the impellor outlet back to the impellor inlet by adding a cylindrical surface to the shroud 1334 to facilitate a sealing at the smaller inlet diameter; and (c) turbulent losses at the outlet 1320 by using a diffuser 1370 machined as part of the primary housing as previously mentioned. These design features assist in increasing the pressure as required but additional torque will be required from the motor meaning that losses remain high, and the steam will nonetheless be superheated to about 122 C or more in spite of best efforts at mitigating the above losses.

Figure 11:
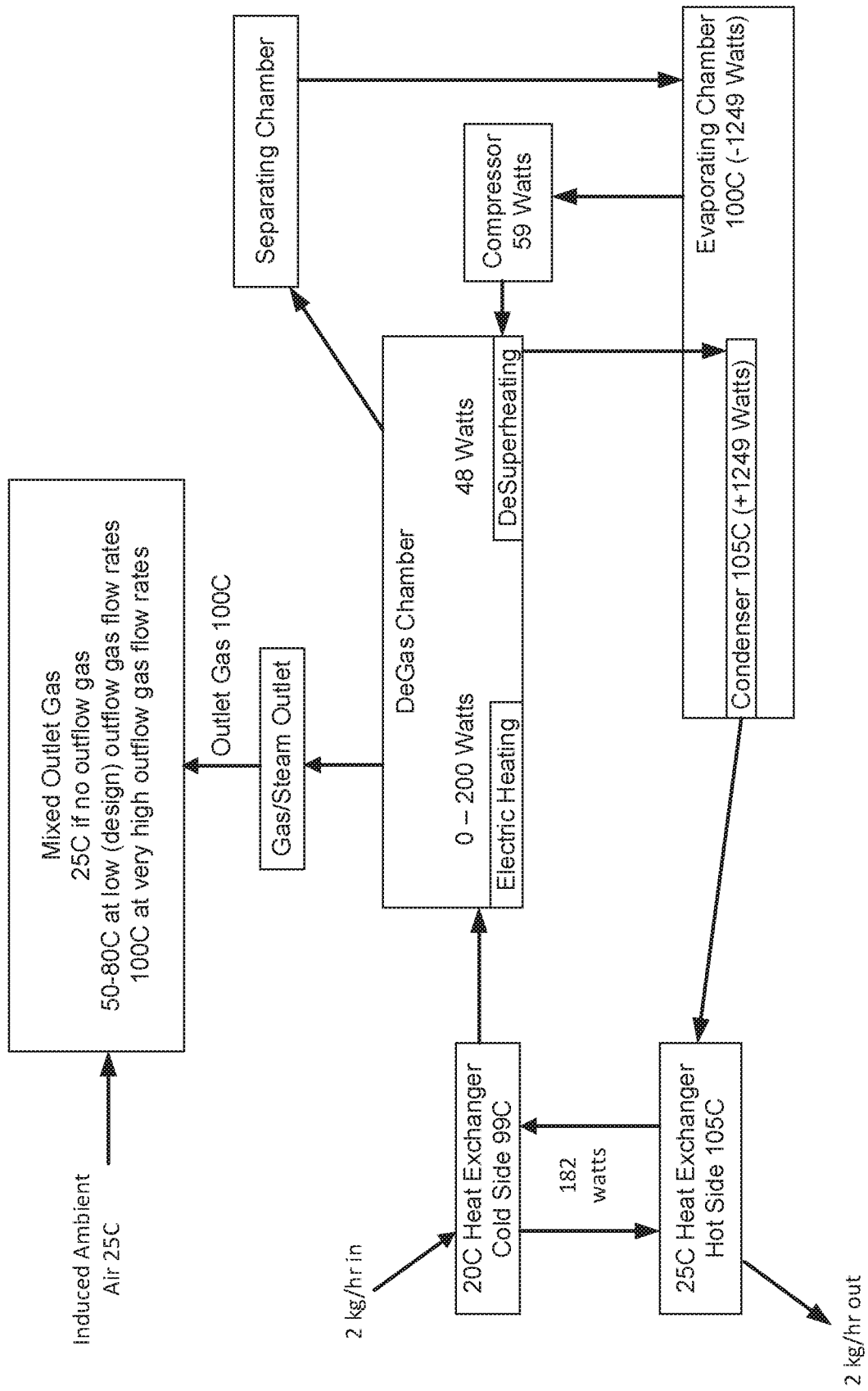
FIG. 11 illustrates schematically the energy exchange and temperature changes occurring as fluid flows through the system according to a preferred embodiment of the invention.

However, the inventor has realised that this energy loss can be advantageously recovered. FIG. 11 illustrates schematically the energy exchange and temperature changes occurring as fluid flows through the system 1000 according to a preferred embodiment of the invention. The outlet vapour from the compressor 1300 is directed through the condenser region, and extended into the heat exchanger/degassing area which also includes an electric heater 1140. The fluid in this area will be at a temperature close to 100 C, which provides a sufficient temperature difference to achieve heat transfer. FIG. 11 shows that the superheat energy (48 W), although only less than 4% of the evaporation energy needed if deployed within the condenser/evaporator heat exchange environment, represents a significant percentage of 182 W energy transfer in the heat exchange environment. This is an important energy consideration. It is also advantageous to assist in the degassing process at this location by boiling the fluid (e.g. water), and thus releasing some steam from its surface in addition to the dissolved gases—this is a further demand on the energy resource available which can partially be offset by the superheat recovery method described.

Although the heater exchanger module 1100 can pre-heat the fluid (e.g. water) to almost 100 C, parasitic losses in the system 1000 require the presence of the electric heater 1140 as a "top-up". In a low power environment, such as battery or solar power, the ability of the superheated vapour to be used in this manner can compensate for the additional energy consumed by the compressor 1300 by substituting this energy for the energy which would otherwise be consumed by the electric heater 1140. The compressor motor power output is about 59 W and using this method, 48 W of the 59 W can be advantageously recovered in this exemplary embodiment.

Start-up—Sterilization and Purging

Start-up from full shut-down of system 1000 (for example when the system 1000 has been opened for inspection or maintenance) will now be described. On start-up, a condensate outlet valve 1012 is open facilitating drainage of any fluid in the system 1000. A water inlet valve is opened (or feed pump 2020 is activated) and remains open until the heater 1140 in chamber 1130 is covered. Once the heater 1140 is covered, the inlet valve is closed (or the feed pump 2020 is deactivated). The heater 1140 is energised until initially the fluid boils and produces vapour. A slight pressure increase in the chamber 1130 causes the vapour to flow into the evaporator-condenser module 1200, through the compressor 1300 (which is inactive) and into the inside of the condenser tube 1220 and from there through the heat exchanger tube 1120 to exit through the condensate outlet valve 1012. Initially a considerable amount of condensate is formed, the thermal mass of the system components in the foregoing steam path and environment are such that approximately 110 kJ of heat energy are required to achieve stable operation—using a 200 W heater this process requires about 10 minutes. The energy requirement to bring the water to the operating level and temperature from that of ambient air requires about 195 kJ or a further 5 minutes.

At the end of the start-up stage, all surfaces having contact with the fluid (vapour or condensate) during normal operation will have been brought to or near to 100 C, and held at that temperature for a number of minutes. In addition, any condensate will either drain to the condensate outlet 1014, or, drain back to the evaporation segregated pool in chamber 1130 of the heat exchanger module 1100. Advantageously, this self-draining feature not found in other such purification systems mitigates the risk of stagnant areas collecting potential contaminants and thus reduces the risk of biofilm growth. The start-up process ensures that all fluid process areas are sterile and provided with an initial degree of flushing. On start-up, the initial quantities of purified fluid produced will also be flushed through the system 1000 to the outlet until trace contaminants are reduced to an acceptable level.

Figure 12:
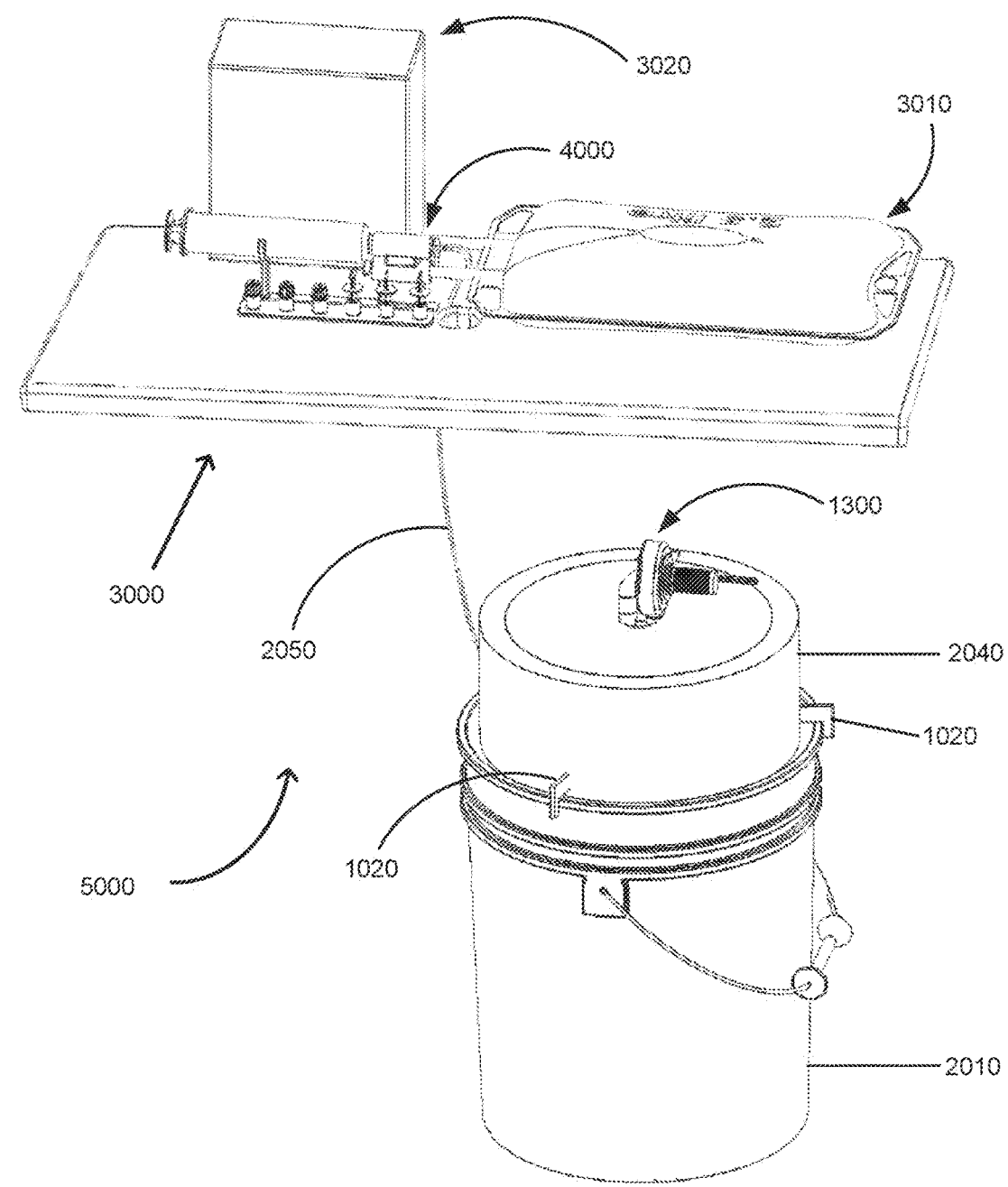
FIG. 12 illustrates a system for preparation of ready-to-use dialysate according to an embodiment of the invention.

These sterilization and flushing procedures can only be effective in single circuit flow regimes with no "uphill" sections or re-entrant features where pockets of condensate can form. The point at which vapour is first "confirmed" can be considered as the start of the purified section. From the compressor outlet 1320 therefore a single conduit is provided for the process stream to follow which is free draining. The sterilisation phase can be extended. Steam will then continue to be produced, and will exit through outlet 1010 and connect via conduit 2050 to provide the sterilisation function at the preparation station 3000 as shown in FIG. 12.

Start-up—Fill Stage

After the system is sterilised and purged as described above, the heat exchanger module 1100 will be at or close to 100 C, and fluid in the evaporator-condenser module 1200 will also be at or close to 100 C.

Transitioning to a steady state operating condition from the sterilising mode described above is achieved by firstly returning the outlet valve 1012 to control of the condensate level sensor 1460 and secondly opening the inlet valve under control (or energising the feed pump 2020) permitting a rise in the water level in the chamber 1130 of the heat exchanger module 1100. Importantly, if the inflow proceeds too rapidly to fill with cold water up to the operating water level within chamber 1130, vapour content in the system 1000 will cool and condense, resulting in a sudden loss of pressure, drawing in more cold water. The rate of inflow will thus be controlled by temperature sensor 1190 until eventually the fluid level sensor 1560 regains control, and the heater 1140 is eventually returned from fully on to modulating control by temperature sensor 1190.

As the mean temperature drops much below 100 C, the steam suddenly condenses, creating a vacuum sucking contaminants in through both the condensate outlet valve 1012 if open, and also through the degas outlet vent. The inventor has realised however that this situation can be avoided by implementing a control system in which incoming fluid flow rate is first controlled to match the ability of heater 1140 to heat the incoming water to boiling point while still maintaining the positive steam pressure. The inventor has further identified that the temperature sensor 1190 used in the degas control system above can be utilised for this additional purpose. Beneficially, adding a second use for the temperature sensor 1190 (the first during normal operation and the second during the preceding fill stage) optimises the efficient use of this component in the system reducing complexity, cost and mass. Ideally, a controller of the system 1000 uses feedback from temperature sensor 1190 to control operation of the inlet control valve/pump 2020 such that a positive outflow of steam is maintained at all times. This requires a higher set point (e.g. 90 C) than is required for normal operation of the system 1000 (requiring e.g. 60 C to 80 C). Thus, as cold fluid is introduced into the system 1000 the steam flow rate will diminish resulting in a lower temperature at sensor 1190 which in turn causes the inlet flow rate to be reduced thereby maintaining a positive steam pressure in the system 1000 at all times. (The heater 1140 is fully energised during this fill period).

This fill stage remains active until the evaporator fluid level sensing means 1460 confirms that it is at normal operational level. Then, the condensate outlet valve 1012 is closed, but the heater 1140 continues to be active. The compressor 1300 is gradually brought to full operating speed. Meanwhile the heater 1140 remains energised until such time as the target condensate level is reached, signifying that the system 1000 is ready to transition to normal operational mode.

As would be apparent to the reader, the inventive system 1000 may be considered akin to a series of closed loops where the same family of sensors and activation devices have their purpose reconfigured to provide a multiplicity of operating modes with a minimum number of components. The inventive system 1000 devised provides a vapour compression distillation means capable of operating with only a single thermally sensitive device (i.e. temperature sensor 1190). System 1000 could be used in a fluid/IV preparation system capable of operating with only one thermal sensor, pump and/or modulating control valve. This arrangement has not be achieved or contemplated by existing prior art systems.

Condensate level is controlled by permitting cooled condensate to exit via the condensate outlet valve 1012. Evaporator water level is controlled by regulating the inflow of unprocessed fluid to the system 1000. The total amount of water produced is dependent on the efficiency of the system 1000, predominantly the efficiency of the evaporator-condenser module loop, which may vary depending on system variables such as for example compressor pressure ratio, and the effect of scaling on the evaporative surfaces. The vapour pressure within the evaporator-condenser module 1200 (and thus of the compressor inlet 1310) should be maintained effectively at atmospheric pressure. However, if the evaporating rate is reduced, for example, by a slight reduction in heat transfer efficiency of the heat exchanger module 1100, there is a possibility of a reduction in pressure below atmospheric, which will cause the water level in the evaporator-condenser housing 1210 to be higher than the level in the chamber 1130 causing the evaporator fluid level sensing means 1460 to create a negative feedback loop, further lowering the evaporation rate and thence an even lower evaporator pressure. This situation is avoided by using the heater 1140 as a supplemental source of energy during operation. The amount of power supplied is then controlled using temperature sensor 1190. If the temperature sensor 1190 detects that the discharge rate of gas and steam is reducing, it increases the heater output, thereby increasing the evaporating rate, and restoring the evaporator pressure to atmospheric, or slightly above, and thus restoring the discharge of gas and steam to the set rate.

This novel use of the fluid level and temperature sensor(s) by the system controller during the start-up purge and fill phases prior to normal operation of the system 1000 enables the system 1000 to self-regulate so that it is ready for and automatically transitions to normal operation when the fluid process areas have been sterilised and filled. This minimises energy and water wastage compared to prior art systems which typically use a fully manual system, or a series of timers to determine that the system 1000 has been sterilised and purged and is ready for normal operation wherein the start-up time duration typically includes an additional time period of "safe margin" during which purified fluid is wasted.

Shut-down—Overnight/Vacuum Mode

When a full shutdown is allowed, external organic compounds enter the system 1000. In a pattern of repeated shutdowns (for example, if shut-down and restarted 3-4 times a day to make dialysate for PD on demand), the risk of biofilm growth is high and likely to occur. On the other hand, the method of "hot standby" as is known in the industry is wasteful of energy. The inventor has therefore devised another mode in which the system 1000 can be shut-down via a short shut-down mode, such as for overnight shutdown or between successive dialysate bag fill operations, as will now be described.

The inlet cold water valve is closed. The heater 1140 is fully energised, and the outlet temperature sensor 1190 is maintained at a temperature close of 100 C. The compressor 1300 is slowed and switched off, and finally the outlet condensate valve 1012 is closed and the heater 1140 is switched off. As the system temperature falls below 100 C, a vacuum develops automatically resulting in closing of the gas outlet 1170 and bleedoff outlet 1274, which preferably include non-return valves. The resulting vacuum can be maintained by an airtight system, and prevents the ingress of organic compounds while non-operational.

On start-up from the overnight/vacuum shut-down, the outlet valve 1012 remains closed until temperature sensor 1190 evidences positive pressure in the system 1000. The rest of the start-up procedure is the same as described above in relation to start-up from full shut-down of system 1000. This method of vacuum shut-down has not been achieved or contemplated by existing prior art systems and advantageously prevents biofilm growth without energy input.

Coupling Device

FIG. 13 shows a coupling device 4000 for use in connecting flow channels 4010 of a plurality of components. When used with the water purification system 1000 discussed above, the coupling device 4000 allows for sterile interconnection of those components. This is ideal for use in preparing ready to use dialysate e.g. for peritoneal dialysis (see system 5000 illustrated in FIG. 12). For example, a PD patient can use the water purification system 1000 to prepare WFI. The PD patient then uses the WFI prepared to dilute dialysate concentrate stored in a receptacle or bag 3010 to prepare ready-to-use (mixed) dialysate. However, the delivery of WFI to the receptacle 3010 requires sterile interconnection since the receptacle or bag 3010 used in PD is placed in a patient's abdomen. Accordingly, it is desirable to provide a coupling device 4000, as shown in FIG. 13, for use in delivery of fluids between the components to ensure that sterility is maintained.

A common problem for PD patients is peritonitis, which is an infection easily caused by even inadvertent contact with an exposed coupling. The inventor has therefore devised the novel coupling device 4000 to ensure that any component being connected through the device 4000 (such as a needle, syringe, conduit or the like) can be brought into a first position where the connected component is attached to the coupling device 4000 forming a sealed chamber but without coupling surfaces of the component and the coupling device 4000 being in contact. In the first position, the sealed chamber is sterilised using ozone or preferably, steam from the water purification system 1000 discussed above. Sterilising the chamber by filling it with steam or ozone also sterilises the coupling surfaces of the components and the inner and outer coupling surfaces 4050, 4060 of coupling device 4000. The components can then be brought into a second position where the coupling surfaces of the components are connected in operational sealing contact. This is achieved without compromising the sterilised environment inside the sealed chamber since no sterilised coupling surface can be contacted when the component is moved from the first position to the second position.

Thus, coupling device 4000 has a plurality of interconnected internal channels 4010 as shown in FIG. 13. Each channel 4010 has a first coupling zone 4020 and a second coupling zone 4030 recessed in the channel 4010 relative to the first coupling zone 4020 to mitigate non-sterile physical contact with the second coupling zone 4030, which includes an outer coupling surface 4050 and an inner coupling surface 4060 of the coupling device 4000. With this construction, each channel 4010 of the coupling device 4000 is configured for two stage connection with a respective component (e.g. syringe 3030, receptacle 3010 and conduit 2050 as shown in FIG. 13); wherein the first stage is a sterilisation stage in which respective ones of the components are in sealing physical contact with the first coupling zone 4020 but not with the second coupling zone 4030; and the second stage is a coupling stage in which the components are physically coupled inside the sterilised device channels 4010 at the sterilised second coupling zone 4030.

Ideally, when the coupling device 4000 is supplied for preparation of dialysate, it includes at least three (preferably four) channels. One channel couples with a component/conduit 2050 supplying purified fluid, another channel couples with a component 3030 supplying concentrated dialysate, such as a syringe, and another channel couples with a component 3010 that is a receptacle or bag 3010 for ready-to-use (mixed) dialysate. A fourth channel may be sealingly closed by a removable cap 4040 applied to the channel opening, or may be coupled to a device supplying steam for sterilisation (for example while all coupling surfaces are in the aforesaid first position). The cap 4040 may have e.g. a tab extension 4042 that provides a grasping (handle) portion for manipulating the coupling device 4000. Ideally, the grasping portion 4042 is in an orientation that enables a user to manipulate the device 4000 with minimal risk of steam burn or contamination of the components during sterilisation because the grasping portion 4042 is outside of the first and second coupling zones 4020, 4030. Once sterilised and the components are brought into the second position, the components are connected and gases, liquids, powders and other fluids can be shared through the coupling device 4000.

In FIG. 13, the coupling device 4000 couples a syringe 3030 loaded with a dose of concentrated dialysate to be mixed with WFI with a conduit 2050 carrying WFI from the fluid purification system 1000 described above, and mixing it for collection in a bag 3010. During sterilisation, conduit 2050 can be used to deliver steam into the channels 4010 of the coupling device 4000 while the attached components are in the first position, so that the steam shrouds the internal second coupling zones 4030, in particular the outer and inner coupling surfaces 4050, 4060, and sterilizes them before the components are brought into physical mating contact with the device 4000 at the second coupling zone 4030.

A similar method can be employed when additional components require sterile coupling, for example, if a concentrate container 3020 is required to be coupled to the syringe 3030 to precharge the syringe 3030 with a single dose of concentrated dialysate. It will be observed that in employing a bag 3010 pre-dosed with a measured concentrate, the same manifold or coupling device 4000 can be used with two ports of the channels 4010 sealed off. It will also be observed that when the patient wishes to couple from the abdomen connection to the dialysate bag 3010 for PD treatment, the same manifold or coupling device 4000 and sterilising method can also be employed. The inventive system 5000, including the fluid purification system 1000 and coupling device 4000, advantageously enables a PD patient to prepare a bag 3010 with ready-to-use (mixed) dialysate in a sterile environment at their home or any other remote location using any water supply available.

Dialysate Preparation System

FIG. 12 illustrates a system 5000 for preparation of ready-to-use dialysate which has a modular purification system 1000 as discussed above contained within a bucket 2010 (see also FIG. 13) which conveniently provides a chamber for storing source water to be purified. FIG. 13 illustrates a feed pump 2020 of system 5000 that includes a pre-filter 2030 which may be matched to local conditions for filtration of source water that may otherwise damage the pump 2020 or contribute to excessive buildup of particular matter within the system 5000. Beneficially, the purification system 1000 can also be used to generate steam at outlet 1010 which can be used to sterilize surfaces, such as those which are connected to mix ready-to-use dialysate via coupling device 4000.

Figure 15:
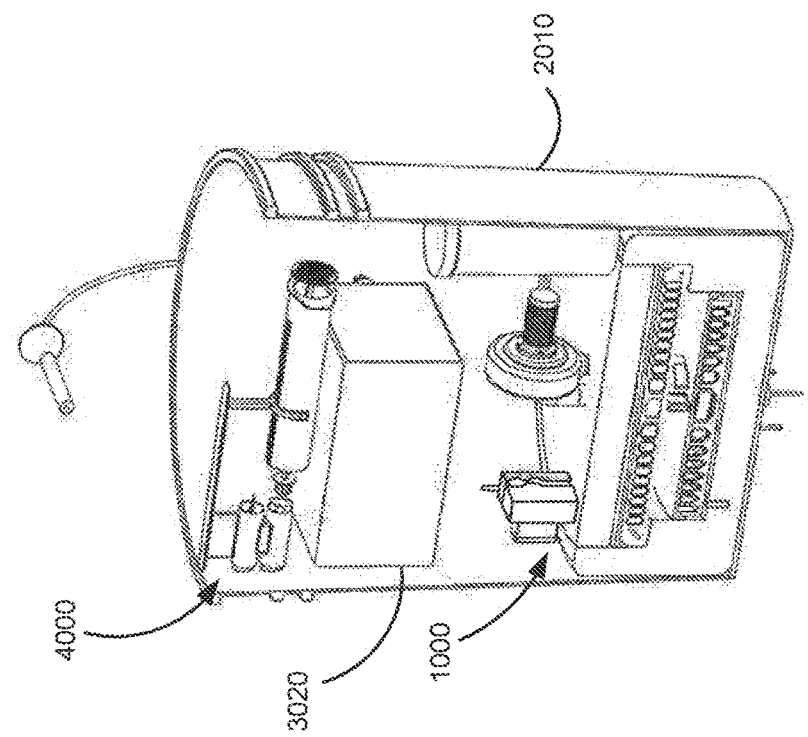
FIG. 15 is a cross-sectional view of components in FIG. 12 showing a fluid purification system in a stored configuration with folded legs and other components positioned within a bucket according to an embodiment of the invention.
Figure 14:
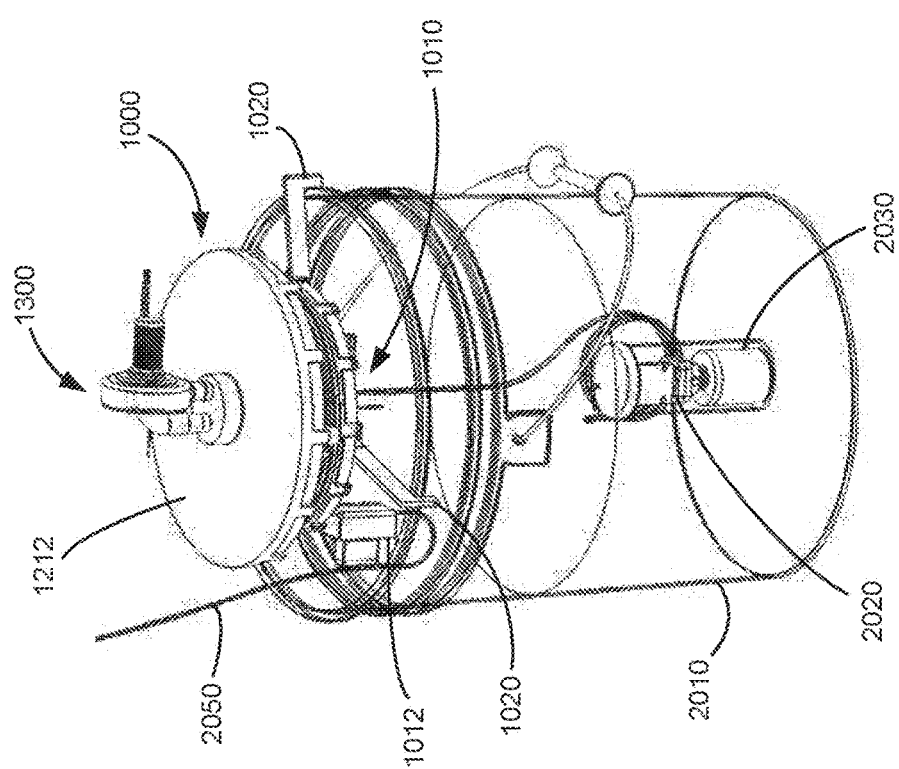
FIG. 14 is an enlarged view of components in FIG. 12 showing a fluid purification system in an operating configuration with extended legs mounted on a top edge of a bucket (transparent to illustrate components and insulating case not shown) according to an embodiment of the invention.

The system 5000 is provided with extending/folding legs 1020 as shown in FIGS. 12 and 14. When folded, the entire purification system 5000 can fit into a container or bucket 2010 as illustrated in FIG. 15 (all in cross-section) in a stored configuration. The bucket 2010 stores the fluid purification system 1000, preparation station 3000 with coupling device 4000 and concentrate container 3020, together with the fluid input pump and filter 2020, 2030. The legs 1020 when extended can be used to support the fluid purification system 1000 on a top rim of the container or bucket 2010 for convenient operation in an operating configuration as shown in FIGS. 12 and 14. Although extending/folding legs are illustrated and described, the system 5000 may include any alternative means known to a person skilled in the art for conveniently mounting and storing the fluid purification system 1000.

The system 5000 as described includes a modular purification system 1000 contained within a bucket 2010. However, the bucket 2010 may be any form of portable carrier such as a container, receptacle or vessel appropriately sized for storing the system 1000 therein. The portable carrier in embodiments of the invention is manually operable for improved access to and mobility of the system components, namely the modular purification system 1000, coupling device 4000 and preparation station 3000. The portable carrier is preferably portable by hand. For example, the bucket 2010 as shown in FIG. 12 includes handles for easily and conveniently moving the bucket 2010 for accessing and assembling the system components.

Removable insulating casing 2040 (see FIG. 12) protects the modules in the fluid purification system 1000 and provides a further mounting or casing for the compressor 1300. The insulating casing 2040 also minimises heat and noise loss to the ambient environment. With the casing 2040 applied to the bucket 2010, the fluid purification system 1000 is compact, portable and robust making it suitable for use in the home, car, RV, or with any source of renewable energy. The provision of a vapour-compression distiller in the form of system 1000 with degas capability and further being portable, preferably by hand, through the container 2010 of system 5000, is an arrangement not achieved or contemplated by prior art systems.

Conduit 2050 provides purified fluid from the bucket 2010, typically in the form of WFI which is transferred to the preparation station 3000. On the preparation station 3000 a pack or bag 3010 may be provided for receiving dialysate concentrate from concentrate container 3020 and WFI through coupling device 4000. It is to be understood, however, that other receptacles for receiving the mixed dialysate may be used such as bottles, tubes and the like.

Although the system 5000 has been described in the context of preparing ready-to-use dialysate, a person skilled in the art would appreciate that system 5000 may be used for treatment of any treatment fluid requiring dilution with purified fluid (e.g. WFI prepared using system 1000) from concentrate, such as intravenous (IV) fluid. The concentrate may include a precursor ingredient or medication such as salt, glucose and/or sodium lactate, as is known for IV or peritoneal administration. Alternatively, the concentrate may include a pharmaceutical grade composition. Advantageously, system 5000 enables preparation of any treatment fluid in a receptacle or bag 3010 under aseptic conditions, from which all air and other contamination are excluded.

Treatment Fluid Preparation System

Figure 16:
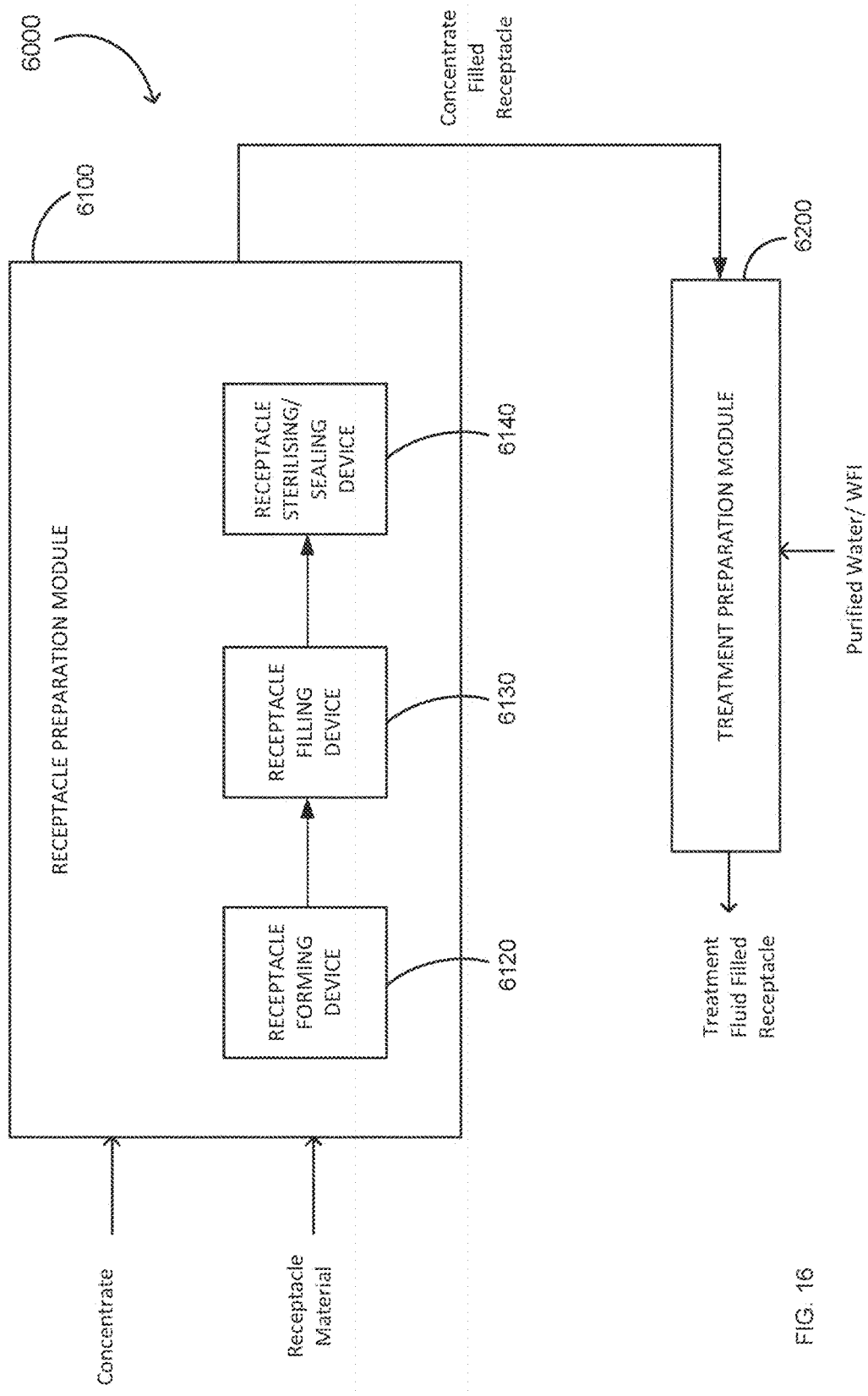
FIG. 16 illustrates a system for preparation of a concentrate filled receptacle and a ready-to-use treatment fluid in the receptacle according to an embodiment of the invention.

FIG. 16 shows a system 6000 for preparation of a receptacle and a ready-to-use treatment fluid in the receptacle. The treatment fluid may include dialysate for a PD patient or more generally preparation of IV or other medication fluids as described above. The problem with such treatment fluid preparation is that large volumes of liquid purified water must be transported from the point of preparation to the point of use by the patient. The transportation and storage of this bulk purified water can be avoided by preparing the purified water at or adjacent to the point of use. The inventor has therefore devised a system 6000 where a sterilised receptacle is formed, filled and sealed with a concentrate (such as a precursor ingredient or medication as described above) in one location, and purified water is added in a second location using aseptic filling means to prepare a treatment fluid in the receptacle ready for administration to a patient.

Referring now to FIG. 16, the system 6000 includes a receptacle preparation module 6100 for forming a receptacle, filling the receptacle with concentrate under sterile conditions and sealing the filled receptacle in preferred embodiments. The system 6000 also includes a treatment preparation module 6200 for supplying purified water or WFI (e.g. from system 1000) to the receptacle under sterile conditions for dilution of the concentrate, thus providing a receptacle having a ready-to-use treatment fluid.

The receptacle preparation module 6100 includes a receptacle forming device 6120, which is supplied with receptacle material such as plastic pellets or tube and adhesive material. The receptacle forming device 6120 cuts an extruded plastic tube and welds both open ends, and incorporates a connection means (e.g. adhesive material) while welding. Preferably, the receptacle forming device 6120 uses blowmoulding technology to form the receptacle as is known to a person skilled in the art. The formed receptacle is then filled with concentrate supplied to the receptacle filling device 6130. A receptacle sterilising/sealing device 6140 is also included which sterilises the filled receptacle by injecting steam into the receptacle and displacing air present. The sterilising/sealing device 6140 then seals the filled and sterilised receptacle.

It is known to use Blow Fill Seal (BFS) technology to form receptacles. The receptacle thus formed is filled with treatment fluid at the point of manufacture of the receptacle. This is disadvantageous in view of the bulk shipping and transportation problem as outlined above. The inventor has addressed this disadvantage by first providing a receptacle forming device 6120 that partially blow-moulds the receptacle, as is known using BFS technology. A concentrate of typically 0.2 to 5 g per litre of volume is then placed in the receptacle using the receptacle filling device 6130. The air in the receptacle is then displaced by injecting steam into the receptacle for sterilisation using the receptacle sterilising/sealing device 6140. Prior to sealing the receptacle, the volume is preferably reduced by collapsing the outside walls. The receptacle walls may be collapsed by, for example, by filling the interior of the receptacle with steam, and then allowing the steam to cool and thus condense creating an internal vacuum. Alternatively, compressed air may be applied to the outside of the receptacle to collapse the outside walls. The receptacle is then sealed by device 6140 using BFS technology in the manner known.

Thus, a sterilised receptacle is provided containing concentrate for the treatment fluid, e.g. IV or dialysate fluid that is packaged in an aseptic manner, from which all air and other contaminants are excluded, and which can be safely transported to the point of use where WFI or pure water can be added to provide a treatment fluid ready for administration. Accordingly, the receptacle preparation module 6100 may be located in a first location, such as a laboratory, a medical preparation plant or factory. The sealed and sterilised receptacle with concentrate can then be transported to a second location, namely the patient's home or other location, such as a hospital or medical clinic, for dilution with purified water to provide a ready-to-use treatment fluid.

The system 6000 also includes a treatment preparation module 6200 that is configured to supply pure water or WFI (e.g. from system 1000) to the filled and sealed receptacle to form a treatment fluid filled receptacle, under sterile conditions. The treatment preparation module 6200 may be located at the second location, e.g. the point of use of the treatment fluid. The receptacle may be provided with a connection feature which can be aseptically pierced to supply the pure water or WFI. In some embodiments, the treatment preparation module 6200 may include a water purification means, such as system 1000, which includes an interconnection means that pierces the receptacle and permits aseptic filling of the receptacle with pure water or WFI. Alternatively, the treatment preparation module 6200 may include the coupling device 4000 of FIGS. 12 and 13 for coupling the filled and sealed receptacle with a conduit 2050 from system 1000 delivering WFI.

The treatment fluid in the receptacle after the treatment preparation module 6200 is ready-to-use for patient administration. The treatment fluid will typically comprise mostly liquid water and between 0.1% to 5% pharmaceutical compounds, such as salt, glucose and/or sodium lactate to name a few, as is known for IV or peritoneal administration, or dialysate for PD.

The above references to "fill", "filling", "filled receptacle" and "filled concentrate receptacle" and the like is to be interpreted as at least partly filling but not necessarily completely filling the receptacle with concentrate. Ideally, the receptacle is only partially filled with the concentrate so as to allow dilution with purified water to provide a ready-to-use treatment fluid.

Where the terms "comprise", "comprises", "comprised" or "comprising" are used in this specification (including the claims) they are to be interpreted as specifying the presence of the stated features, integers, steps or components, but not precluding the presence of one or more other features, integers, steps or components or group thereof.

It is to be understood that various modifications, additions and/or alterations may be made to the parts previously described without departing from the ambit of the present invention as defined in the claims appended hereto.

It is to be understood that the following claims are provided by way of example only, and are not intended to limit the scope of what may be claimed in any future application. Features may be added to or omitted from the claims at a later date so as to further define or re-define the invention or inventions.

What is claimed is:

1. A system for purifying incoming fluid, the system being modular and comprising:
    (a) a heat exchanger module having a first housing containing a thermally conductive heat exchanger tube;
    (b) an evaporator-condenser module having a second housing containing a condenser tube; and
    (c) a compressor;
    wherein the system is configured to facilitate passive drainage of the purified fluid for collection, and wherein the above components are arranged in a stacked configuration to facilitate gravitational flow of the purified fluid such that the purified fluid drains passively for collection, wherein:
    the first housing defines a first chamber containing a heater and receiving a conductive tube carrying pressurized vapor from the compressor;
    the conductive tube has a first vapor outlet to deliver pressurized vapor into the condenser tube of the evaporator-condenser module; and
    the conductive tube has a second vapor outlet for injecting pressurized vapor into the first chamber to facilitate degassing of fluid in the first chamber.

2. The system according to claim 1, wherein the conductive tube and connections between the modular components are disposed vertically to minimize fluid retention in the system during gravitational flow.

3. The system according to claim 1, wherein the thermally conductive heat exchanger tube is a coiled tube, which is a single continuous tube arranged within the first housing in a planar coil.

4. The system according to claim 1, wherein the condenser tube is a conductive coiled or folded condenser tube arranged within the second housing such that in operation, the condenser tube is partially immersed in fluid in the second housing.

5. The system according to claim 4, wherein the condenser tube is a single continuous tube arranged within the second housing in a planar coil.

6. The system according to claim 4, wherein the evaporator-condenser module includes one or more nozzles configured to inject pressurized vapor from the compressor into the second housing.

7. The system according to claim 6, wherein a plurality of the nozzles are spaced around a periphery of the condenser tube within the second housing and situated below a fluid level in the housing during operation.

8. The system according to claim 4 further including one or more radially extending fluid flow channels in the housing of the evaporator-condenser module that are configured to encourage fluid to return from the center of the housing to an outer region of the housing.

9. The system according to claim 1, wherein one or both of first and second housings having a lower housing portion and an upper housing portion that are releasably couplable so as to facilitate access to surfaces of the modules.

10. The system according to claim 1, wherein the heat exchanger module defines an incoming fluid flow channel formed by a void in the first housing.

11. The system according to claim 10, wherein the void is positioned between an upper housing portion, a thermally conductive coiled tube and a lower housing portion of the heat exchanger module.

12. The system according to claim 11, wherein the upper housing portion includes a grooved channel that together with the lower housing portion forms the void, which is confined by the outside of the thermally conductive coiled tube.

13. The system according to claim 12, wherein the thermally conductive coiled tube and grooved channel are spiral-shaped such that the void is arranged as a closed spiral channel.

14. The system according to claim 1 wherein the first chamber includes a common gas discharge exit that combines gas from degassing that occurs in the first chamber and gas output from the pressurized vapor during operation of the system.

15. The system according to claim 14, wherein the first chamber, a portion of the heat exchanger module and a portion of the evaporator-condenser module are integrally molded such that they share common housing components.

16. The system according to claim 1 wherein the first chamber includes a fluid level sensor to detect a fluid level covering the heater.

17. The system according to claim 16 wherein the fluid level sensor is operatively connected to a fluid inlet controller configured to control the rate of incoming fluid flow into the heat exchanger module.

18. The system according to claim 1 wherein the conductive tube is vertically disposed.

19. The system according to claim 1 wherein the conductive tube extends vertically through the evaporator-condenser module to the heat exchanger module.

20. A system for purifying incoming fluid, the system being modular and comprising:
(a) a heat exchanger module having a first housing containing a condenser tube;
(b) an evaporator-condenser module having a second housing containing a condenser tube; and
(c) a compressor;
wherein the heat exchanger module defines an incoming fluid flow channel formed by a void in the first housing of the heat exchanger module, wherein:
the first housing defines a first chamber containing a heater and receiving a conductive tube carrying pressurized vapor from the compressor;
the conductive tube has a first vapor outlet to deliver pressurized vapor into the condenser tube of the evaporator-condenser module; and
the conductive tube has a second vapor outlet for injecting pressurized vapor into the first chamber to facilitate degassing of fluid in the first chamber.

21. A system for purifying incoming fluid, the system being modular and comprising:
(a) a heat exchanger module having a first housing containing a thermally conductive heat exchanger tube;
(b) an evaporator-condenser module having a second housing containing a condenser tube arranged within the second housing; and
(c) a compressor;
wherein the evaporator-condenser module includes a thermally conductive condenser tube arranged within a housing of the evaporator-condenser module such that in operation, the condenser tube is partially immersed in fluid in the second housing, wherein:
the first housing defines a first chamber containing a heater and receiving a conductive tube carrying pressurized vapor from the compressor;
the conductive tube has a first vapor outlet to deliver pressurized vapor into the condenser tube of the evaporator-condenser module; and
the conductive tube has a second vapor outlet for injecting pressurized vapor into the first chamber to facilitate degassing of fluid in the first chamber.

* * * * *